US012778518B2

(12) United States Patent
Vardoulis et al.

(10) Patent No.: US 12,778,518 B2
(45) Date of Patent: Nov. 3, 2026

(54) STROKE MONITOR

(71) Applicant: Zeit Medical, Inc., Redwood City, CA (US)

(72) Inventors: Orestis Vardoulis, San Francisco, CA (US); Urs H. Naber, Redwood City, CA (US); Stylianos Kyriacou, Redwood City, CA (US)

(73) Assignee: Zeit Medical, Inc., Redwood City, CA (US)

( * ) Notice: Subject to any disclaimer, the term of this patent is extended or adjusted under 35 U.S.C. 154(b) by 0 days.

(21) Appl. No.: 18/870,355

(22) PCT Filed: May 30, 2023

(86) PCT No.: PCT/US2023/023848
§ 371 (c)(1),
(2) Date: Nov. 27, 2024

(87) PCT Pub. No.: WO2023/235304
PCT Pub. Date: Dec. 7, 2023

(65) Prior Publication Data

US 2025/0169768 A1 May 29, 2025

Related U.S. Application Data

(60) Provisional application No. 63/365,602, filed on May 31, 2022.

(51) Int. Cl.
*A61B 5/00* (2006.01)
*A61B 5/31* (2021.01)
*A61B 5/369* (2021.01)

(52) U.S. Cl.
CPC .............. *A61B 5/7282* (2013.01); *A61B 5/31* (2021.01); *A61B 5/369* (2021.01); *A61B 5/4842* (2013.01);
(Continued)

(58) Field of Classification Search
CPC ......... A61B 5/7282; A61B 5/31; A61B 5/369; A61B 5/4842; A61B 5/7267; A61B 5/7275; A61B 5/746
See application file for complete search history.

(56) References Cited

U.S. PATENT DOCUMENTS 6,360,122 B1 3/2002 Fischell et al.
6,385,486 B1 5/2002 John et al.
(Continued)

FOREIGN PATENT DOCUMENTS

CN 106333682 A 1/2017
EP 2682053 A1 1/2014
(Continued)

OTHER PUBLICATIONS

Hand, Peter J., et al. "Distinguishing between stroke and mimic at the bedside: the brain attack study." Stroke 37.3 (2006): 769-775. (Year: 2006).*

(Continued)

*Primary Examiner* — Andrey Shostak
(74) *Attorney, Agent, or Firm* — Schwegman Lundberg & Woessner, P.A.

(57) ABSTRACT

A wearable real-time stroke detector apparatus can be configured to be coupled to one or more EEG skin electrodes located on a subject for performing real-time stroke detection. This can include signal processor circuitry. Power spectral density (PSD) circuitry receive an acquired EEG signal acquired via a channel coupled to a skin electrode of the one or more EEG skin electrodes. The PSD circuitry can compute a monitored PSD EEG signal using the acquired EEG signal. Baseline-adjustment circuitry form a baseline-adjusted monitored PSD EEG signal using the monitored PSD EEG signal and the baseline PSD EEG signal. Classifier circuitry can use a trained model to classify a temporal shift in the baseline-adjusted monitored PSD EEG signal,
(Continued)

over a specified range of frequencies, to produce an alert indicating Detected Stroke based on the classified temporal shift as determined by the classifier circuitry using the trained model.

21 Claims, 11 Drawing Sheets

(52) U.S. Cl.
CPC .......... *A61B 5/7267* (2013.01); *A61B 5/7275* (2013.01); *A61B 5/746* (2013.01)

(56) References Cited

U.S. PATENT DOCUMENTS

| | | | | |
|---|---|---|---|---|
| 6,473,639 | B1 | 10/2002 | Fischell et al. | |
| 6,810,285 | B2 | 10/2004 | Pless et al. | |
| 6,985,769 | B2 | 1/2006 | Jordan | |
| 7,373,199 | B2 | 5/2008 | Sackellares et al. | |
| 8,108,033 | B2 | 1/2012 | Graves et al. | |
| 8,594,779 | B2 | 11/2013 | Denison et al. | |
| 8,884,767 | B2 | 11/2014 | Kidmose | |
| 9,480,845 | B2 | 11/2016 | Harris et al. | |
| 9,532,748 | B2 | 1/2017 | Denison et al. | |
| 2005/0203366 | A1 | 9/2005 | Donoghue et al. | |
| 2010/0145176 | A1 | 6/2010 | Himes | |
| 2011/0245707 | A1 | 10/2011 | Castle et al. | |
| 2012/0150545 | A1* | 6/2012 | Simon | A61B 5/6804 704/270 |
| 2014/0031711 | A1* | 1/2014 | Low | A61B 5/4076 600/544 |
| 2018/0353084 | A1 | 12/2018 | Wainright et al. | |
| 2021/0030299 | A1* | 2/2021 | Naber | A61B 5/7267 |
| 2021/0251497 | A1* | 8/2021 | Schulhauser | A61B 5/0205 |
| 2022/0044821 | A1* | 2/2022 | Eichler | G16H 50/20 |
| 2022/0257149 | A1* | 8/2022 | Ralston | A61B 5/1126 |

FOREIGN PATENT DOCUMENTS

| | | | |
|---|---|---|---|
| WO | WO-2004096040 | A1 | 11/2004 |
| WO | WO-2007150003 | A2 | 12/2007 |
| WO | WO-2014172775 | A1 | 10/2014 |
| WO | WO-2018057667 | A1 | 3/2018 |
| WO | WO-2018124841 | A1 | 7/2018 |
| WO | WO-2019018291 | A1 | 1/2019 |
| WO | WO-2023235304 | A1 | 12/2023 |

OTHER PUBLICATIONS

International Application Serial No. PCT/US2023/023848, International Search Report mailed Aug. 31, 2023, 5 pgs.

International Application Serial No. PCT/US2023/023848, Written Opinion mailed Aug. 31, 2023, 6 pgs.

Kalahasty, Rohan, et al., "StrokeSight: A Novel EEG-Based Diagnostic System for Strokes Using Spectral Analysis and Deep Learning", arxiv.org, Cornell University Library, 201 Olin Library Cornell University Ithaca, NY 14853,, (Mar. 27, 2022), 7 pgs.

Park, Wanjoo, et al., "Assessment of Cognitive Engagement in Stroke Patients From Single-Trial EEG During Motor Rehabilitation", IEEE Transactions on Neural Systems and Rehabilitation Engineering, IEEE, USA, vol. 23, No. 3, (May 1, 2015), 12 pgs.

Qureshi, Arooj Ahmed, et al., "Ischemic stroke detection using EEG signals", Computer Science and Software Engineering, IBM Corp, PO Box 10659 Riverton, NJ08076-0659USA, (Oct. 29, 2018), 8 pgs.

* cited by examiner

STROKE MONITOR

CLAIM OF PRIORITY

This application is a U.S. National Stage Filing under 35 U.S.C. 371 from International Application No. PCT/US2023/023848, filed on May 30, 2023, and published as WO 2023/235304 A1 on Dec. 7, 2023, which claims the benefit of priority of Vardoulis et al. U.S. Provisional Patent Application Ser. No. 63/365,602, filed on 31 May 2022, entitled STROKE MONITOR, each of which is hereby incorporated by reference herein in its entirety.

TECHNICAL FIELD

This document pertains generally, but not by way of limitation, to medical diagnostics and more particularly, but not by way of limitation to stroke detection and monitoring systems, devices, and methods.

BACKGROUND

A cerebrovascular accident (CVA) or stroke refers to the loss of brain function due to inadequate oxygen supply, most commonly due to disruption in blood perfusion to the brain. With lack of oxygenation, there is subsequent energy depletion, resulting in loss of cellular membrane potential and subsequent depolarization of neurons and glial cells. Within minutes, there is irreversible damage to the ischemic core tissue region that is otherwise supplied by inline blood flow. The surrounding unstable tissue region, termed the penumbra, is rendered dysfunctional by restricted blood supply and oxygen, but retains marginal energy metabolism due to collateral blood flow. This tissue is potentially salvageable if proper blood flow can be restored. But the collateral blood flow is unstable and, over time, will be inadequate for neuronal survival. It is well understood that time to treatment inversely correlates with better outcomes. With each elapsed second of continued ischemia, the ischemic core tissue region grows, including more of the penumbra until there is no salvageable tissue left. The penumbra is the target of current revascularization therapy, as this at-risk tissue can recover function if given restoration of oxygen and energy supply.

Stroke can be categorized as ischemic or hemorrhagic. Ischemic stroke, which constitutes roughly 87% of all strokes, is mainly secondary to atherothrombotic, embolic, and small-vessel diseases. Less common causes include coagulopathies, vasculitis, dissection, hypotension and venous thrombosis. Hemorrhagic stroke occurs secondary to vessel rupture leading to either an intracerebral or subarachnoid hemorrhage, with direct damage of the surrounding tissue as well as impairment of blood flow to the tissues distal to the hemorrhage that may cause cerebral ischemia.

Stroke is the fifth leading cause of death in the United States and the second leading cause of death worldwide. In the United States, there are roughly 795,000 strokes annually and 7 million stroke survivors—a number expected to grow rapidly as the population ages. Stroke survivors suffer from substantial morbidity. Stroke is the leading cause of long-term disability in the United States currently accounting for roughly $72 billion in direct medical care. The AHA estimates the annual direct medical cost of stroke to increase to as much as $180 billion by 2030.

As outlined above, functional outcomes, survival, and cost of care all improve the earlier that blood flow can be restored to the tissue at risk. "Time is brain" is a widely adopted maxim, and door to needle times have become a quality marker for stroke centers around the world. Delays can happen at multiple points during the stroke care continuum. First, the patient or someone around the patient needs to identify the occurrence of the stroke and activate help. Second, the patient needs to be transported to the appropriate treatment facility depending on the patient's eligibility for thrombolysis and thrombectomy. Third, the patient needs to be appropriately triaged and diagnosed (e.g., stroke assessment protocol NIHSS, imaging protocol, etc.) before being provided with treatment. Unfortunately, despite public awareness campaigns, the majority of delays happen due to inadequate recognition of the occurrence of stroke or other circumstances in the patient's home. A large percentage of patients present to the hospital at a time too late after stroke occurrence for effective treatment.

An example of stroke detection using implantable electrodes is mentioned in Naber et al. U.S. Patent Pub. No. 2021/0030299 A1.

SUMMARY

The present inventors have recognized, among other things, that stroke detection and local or remote monitoring (e.g., using external skin electrodes such as can be included in a headband or skull-cap that can be worn by a patient) can be challenging, for example, due to one or more confounding factors, such as medication status, sleep state, or the occurrence of one or more stroke mimics such as migraine, post-migraine, seizure, post-seizure, post-ictal or other stroke mimic.

This document describes, among other things, stroke monitoring devices and methods that can help address such confounding factors and improve accuracy of stroke detection and monitoring, including by performing particular baseline-adjustment techniques on Power Spectral Density (PSD) EEG signals such as can be received via multiple channels from multiple skin electrodes located on a subject. After performing such baseline adjustment, classifier circuitry can use a trained learning model to classify a temporal shift in the baseline-adjusted monitored PSD EEG signal, such as over a specified range of frequencies. The classification can be used to produce an alert indicating detected stroke based on the classified temporal shift as determined by the classifier circuitry using the trained model.

This Summary is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

This document describes, among other things, a stroke detector and monitor. The stroke detector and monitor can permit single-channel or multi-channel EEG signal acquisition from corresponding external skin electrodes. Analog and digital pre-processing can be performed on such one or more acquired EEG signals. The pre-processed EEG signals can be converted to a power spectral density (PSD) EEG signal. Baseline-adjustment can be performed on the PSD EEG signal. The baseline-adjusted PSD EEG signal can be used by classifier circuitry. A temporal shift in the baseline-adjusted monitored PSD EEG signal can be analyzed and classified, such as over a specified range of frequencies. The classifier can include a trained learning model, and the resulting classification can be used to produce an alert indicating detected stroke, which can be based on the classified temporal shift as determined by the classifier circuitry using the trained model.

Figure 1:
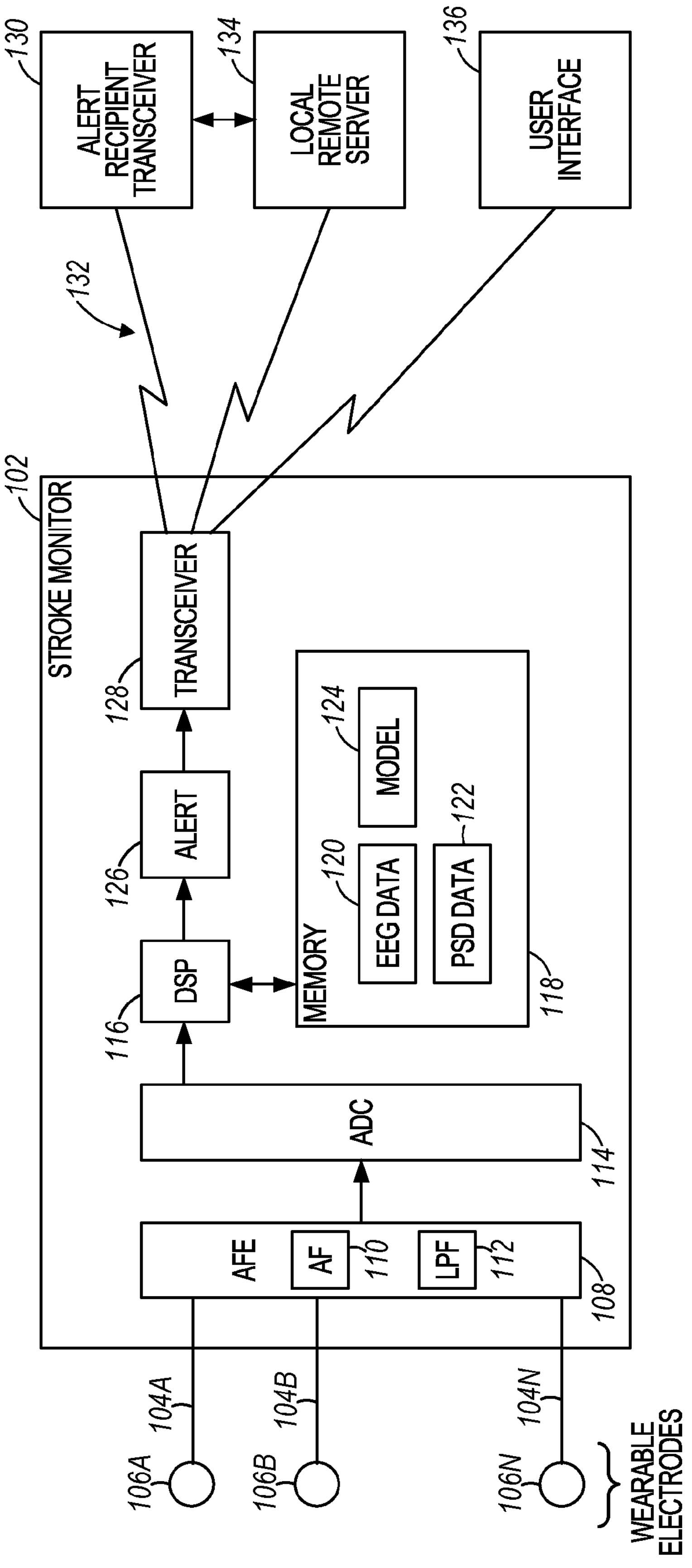
FIG. 1 is a block diagram showing an example of portions of a stroke monitor system.

FIG. 1 is a block diagram showing an example of portions of a stroke monitor system 100. The stroke monitor system 100 can include a stroke monitor device 102. The stroke monitor device 102 can include an electronics unit that can be coupled, such as via one or more channels 104, to corresponding external EEG skin electrodes 106 (e.g., 5-10 skin electrodes and corresponding channels). For example, the external EEG skin electrodes 106 can be worn on a garment, such as a headband, cap, sleeve, or other suitable carrier. Additionally or alternatively, the external EEG skin electrodes 106 can be directly affixed to the skin on the head or other suitable body location of the human or other animal subject being monitored for the occurrence of a stroke. Extending from the external EEG skin electrodes 106, corresponding electrical conductors can provide individual channels 104 that are respectively coupled to analog front end (AFE) circuitry 108 in the stroke monitor device 102. One or more reference "ground electrodes" can also be provided, and either shared between different signal electrodes of different individual channels 104, or co-located with respective signal electrodes of different individual channels. The one or more reference or ground electrodes can be provided corresponding respective electrical conductors that are respectively coupled to the AFE circuitry 108 in the stroke monitor device 102.

The AFE circuitry 108 can include single channel or multi-channel analog signal pre-processing circuitry. For example, the AFE circuitry 108 can include artifact filter AF circuitry 110 and noise suppression lowpass or bandpass filter LPF/BPF circuitry 112. The artifact filter AF circuitry 110 can be configured to be coupled to the external EEG skin electrodes 106 such as to receive a raw EEG signal from the external EEG skin electrodes 106, from which the AF circuitry 110 can help remove or attenuate a non-EEG signal artifact. For example, such removed or attenuated non-EEG signal artifacts can include at least one of a high skin-electrode impedance artifact (such as due to poor placement or poor skin contact of the external EEG skin electrodes 106), a muscle activation signal (e.g., electromyography (EMG) signal) artifact, or an eye movement signal artifact. The AF circuitry 110 can operate such as to produce a resulting artifact-filtered EEG signal from the raw EEG signal. In the resulting artifact-filtered EEG signal, one or more such signal artifacts have been removed or attenuated.

The LPF/BPF circuitry 112 can include one or more inputs that can be coupled to the AF circuitry 110, such as to receive the one or more respective artifact-filtered EEG signals. The noise suppression lowpass or bandpass filter LPF/BPF circuitry 112 can be configured to remove or attenuate high frequency noise or other signal content outside of the frequency regions of interest for stroke detection. For example, such high frequency noise can include one or more of AC utility line noise (e.g., 60 Hz or harmonics thereof) or switching power supply line noise or other noise source, such as noise from vibration from a CPAP device also being used by the same patient, such as while sleeping. For example, the noise suppression lowpass or bandpass filter LPF/BPF circuitry 112 can include a single pole or higher order filter having a lowpass cutoff frequency pole at or near 20 Hz, frequencies above which are removed or attenuated. The noise suppression lowpass or bandpass filter LPF/BPF circuitry 112 can include a single channel or multi-channel output that can provide a noise-filtered artifact-filtered EEG signal as the acquired EEG signal for use by subsequent signal processing circuitry. The LPF/BPF circuitry 112 can also serve as an anti-aliasing filter (AAF) for subsequent analog-to-digital conversion.

The lowpass filter LPF/BPF circuitry 112 can be configured as bandpass filter BPF circuitry that can also include a single pole or higher order highpass filter HPF, such as providing a HPF cutoff frequency pole at or near 0.1 Hz or 1.0 Hz, for example. This HPF can help reduce or attenuate frequencies lower than the HPF cutoff frequency, such as to help reduce an effect of offset or low frequency drift in the raw EEG signal being acquired by one or more of the external EEG skin electrodes 106.

An analog-to-digital converter ADC 114 can receive the single channel or multiple channel noise-filtered artifact-filtered EEG signal output from the LPF/BPF 112 of the AFE 108. The analog-to-digital converter ADC 114 can employ a suitable sample rate (or oversample rate) to perform analog-to-digital conversion of the one or more channels from corresponding skin electrodes 106. The analog-to-digital conversion can produce single channel or multiple channel digital output values of the noise-filtered artifact-filtered EEG signal for further signal processing and analysis. For example, such further signal processing and analysis can be performed by digital signal processor DSP circuitry 116, such as described further herein.

The digital signal processor DSP circuitry 116 can include single or multiple channel inputs arranged to receive the single channel or multiple channel digitized noise-filtered artifact-filtered EEG signal from the ADC 114. The digital signal processor DSP circuitry 116 can include or be coupled to memory circuitry 118. The memory circuitry 118 can include EEG data storage 120, such as for storing one or more channels of the digitized noise-filtered artifact-filtered EEG data, either in uncompressed form or after compression using a signal compression algorithm. The memory circuitry 118 can include PSD EEG data storage 122, such as for storing power spectral density PSD EEG data such as described herein. The memory circuitry 118 can also store one or more specified calibration or data compression/decompression or other parameters, such as for the ADC 114, for the transceiver 128, or the like. For example, the memory circuitry 118 can store parameters that can include one or more compression/decompression parameters or unique encryption keys, such as for used in compressing or decompressing data or encrypting communications to or from the device 102 via the transceiver 128.

The memory circuitry 118 can include learning model representation storage, such as for storing information associated with an artificial intelligence (AI) or machine learning (ML) or other statistical or other learning model 124 or representation thereof. The memory 118 can include training software 125, such as executable or performable at the stroke device 102 for training the learning model 124, such as using a training data set, or the model 124 can be trained separately locally or remotely, such as using another computing device, and downloaded to the memory 118 of the stroke device 102. Alternatively, the model 124 can be trained and stored separately, locally or remotely, such as in an example in which data is streamed or otherwise communicated from the stroke detection device 102 for auxiliary local or remote signal-processing for alert generation and patient or caregiver notification.

Such a learning model 124 can be used by a local or remote stroke alert generator 126, such as can be included in or coupled to the digital signal processor DSP circuitry 116. For example, a stroke alert generated by the stroke alert generator 126 can be communicated to a wireless or other onboard or auxiliary local communications transceiver 128. The onboard or local auxiliary communications transceiver 128 can transmit the alert to an alert recipient transceiver 130. For example, the alert recipient transceiver 130 can include one or more of an emergency services provider (e.g., ambulance or Emergency Medical Technician or "911" assistance call service) or a medical or other caregiver, such as can be alerted via a mobile telephony communications network 132 or using another communications modality or protocol. In an example, the alert can optionally be provided to an "on call" neurophysiologist, who can examine the patient data, can optionally conduct an immediate or rapid telemedicine or videoconference visit or other clinical examination with the patient, and the "on call" neurologist can then determine whether to place a call for immediate assistance to the emergency services provider. Such patient data examination by a trained "on call" neurophysiologist can be performed in the time-domain (e.g., before being converted into PSD EEG signal data), such as where the trained neurophysiologists are more comfortable in assessing the single electrode time domain tracings than the PSD EEG signal data. Additionally or alternatively, such patient data examination by an appropriately-trained on-call neurophysiologist can also be performed in the frequency-domain, either before or after baseline-adjusting.

Additionally or alternatively, the onboard or local auxiliary communications transceiver 128 can communicate the alert to a local or remote server system 134 of a proprietary or other service provider, which can then contact the emergency services provider or the medical or other caregiver. In response to receiving the alert, someone other than the subject is enabled to assist the subject in seeking and rendering prompt medical assistance and treatment. This can help avoid or reduce post-stroke damage that might otherwise occur. The local or remote server system 134 can also be used to perform training of the model 124, such as based upon data received from the stroke device 102 of a particular patient, based upon population-based data, such as from other stroke devices 102 of other patients, or both. The trained model 124 can then optionally be manually or automatically pushed or downloaded to a particular stroke device 102, or data from a particular stroke device 102 can be streamed or otherwise communicated to a remote hub for signal-processing and analysis, such as can include using the trained model at the remote hub.

The onboard or local auxiliary communications transceiver 128 can also be configured to communicate, such as via the mobile telephony communications network 132, Bluetooth, or other modality, with a user interface 136. For example the user interface 136 can include a mobile phone application or the like. The user interface 136 can be used by the subject to display or tag data (or information derived from data) or to provide input to the digital signal processor DSP circuitry 116 about auxiliary information that may be relevant or important to performing stroke detection and monitoring (e.g., to report one or more symptoms associated with stroke or a stroke-mimic that does not constitute stroke, to report prothrombin (INR) or medication status, or other health information of the subject).

The user interface 136 can also be used to allow the end-user or a caregiver to set up or re-configure the electronics unit of the stroke detector device 102, such as with user preferences that can include a type of push notifications, a list of emergency contacts and individualized protocols for receiving a stroke-detected alert, preferred hospital and health care provider information, health insurance information, a list of medications being taken regularly and their dosages and frequencies, and medical history information, which can include a history of stroke events and a clinical picture thereof, among other things.

The user interface 136 can include or be coupled to one or more other auxiliary health monitoring applications or devices (for example, blood pressure monitor, continuous glucose monitoring device, continuous or ambulatory ECG device, diet or exercise applications, activity monitor, fall sensor, gait sensor, among other things), such as which can communicate information to the stroke monitor device 102 that can be useful in stroke monitoring and detection.

Figure 2:
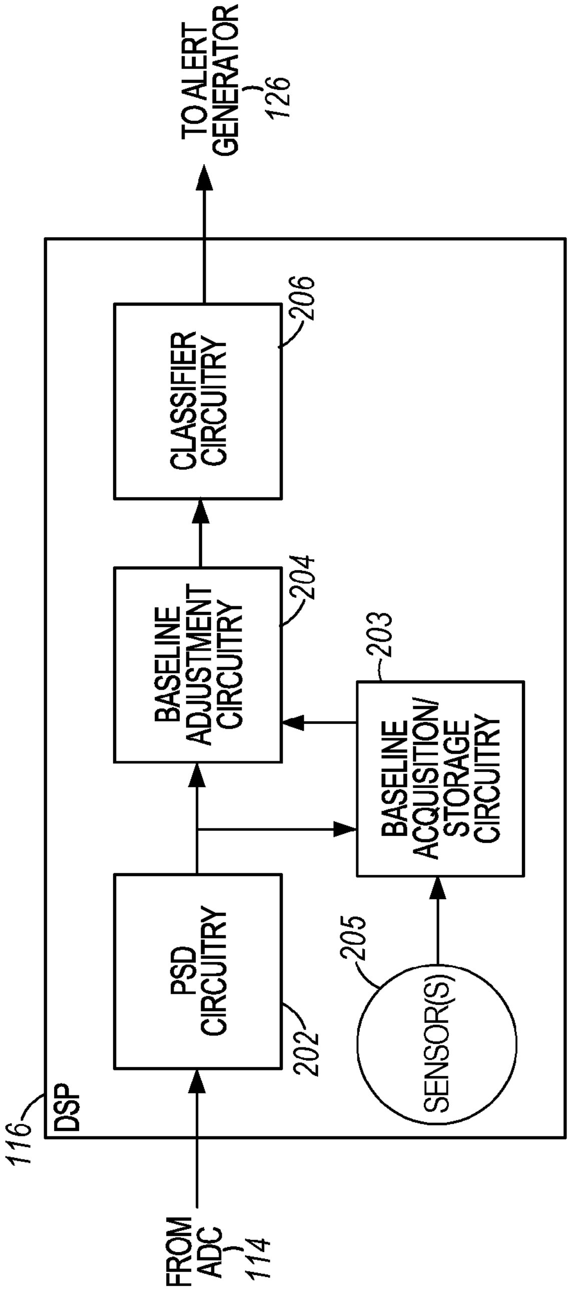
FIG. 2 is a block diagram showing an example of portions of the digital signal processor DSP circuitry in more detail.

FIG. 2 is a block diagram showing an example of portions of the digital signal processor DSP circuitry 116 in more detail. In FIG. 2, the digital signal processor DSP circuitry 116 can include Power Spectral Density PSD circuitry 202. The Power Spectral Density PSD circuitry 202 can include single or multi-channel inputs receiving corresponding digital values from the analog-to-digital converter ADC 114, such as representing the various channels of pre-processed signals from the various EEG electrodes 106. The Power Spectral Density PSD circuitry 202 can convert such digitized signal values from the time-domain into the frequency-domain, such as by performing a Fast Fourier Transform (FFT) (or other transform such as a wavelet transform) using FFT transform or other transform circuitry included in the Power Spectral Density PSD circuitry 202. In this way, a pre-processed monitored digitized PSD EEG signal over a specified range of frequencies, e.g., 0.1 Hz or 1.0 Hz through 20 Hz or 30 Hz or 64 Hz can be determined. In an illustrative example, a spectral resolution, within the specified range, can be established by spectral bins, each between 0.1 Hz to 1 Hz, spanning the overall specified frequency range, e.g., 0.1 Hz to 64 Hz.

Figure 3:
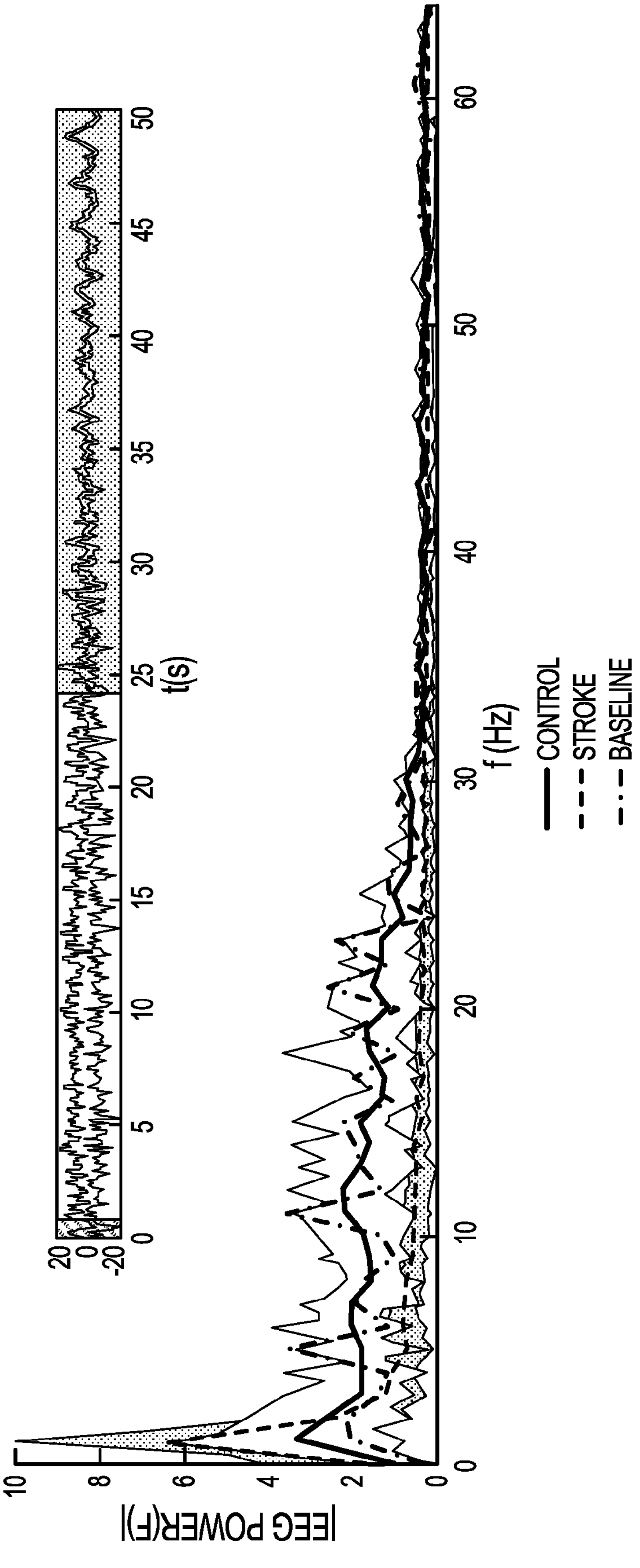
FIG. 3 shows an illustrative example of a pre-processed PSD EEG spectral signal data, graphing EEG signal power as a function of frequency in Hz, which is shown in FIG. 3 before any baseline adjustment is performed.

FIG. 3 shows an illustrative example of pre-processed PSD EEG spectral signal data, graphing EEG signal power as a function of frequency in Hz, shown in FIG. 3 before any baseline adjustment. FIG. 3 shows an example of such PSD EEG spectral data acquired from a particular subject during a control time period (blue) immediately preceding a transition to a stroke, with PSD EEG spectral data acquired from a particular subject during a post-stroke time period (red), and stored baseline PSD EEG spectral data acquired from the subject shown in green. As can be seen in FIG. 3, in the presence of ischemia or hemorrhage with an occurrence of stroke, overall EEG signal power drops, and there are significant changes in the EEG power distribution over a specified frequency range of interest (e.g., 0-30 Hz). However, baseline adjustment can be useful for stroke detection, as explained below.

In FIG. 2, Baseline-Adjustment circuitry 204 can also be included in the digital signal processor DSP circuitry 116. For example a single channel or multiple channels of the PSD EEG signal produced by Power Spectral Density PSD circuitry 202 can be provided to the Baseline-Adjustment circuitry 204, which can determine a relative or normalized "baseline-adjusted" PSD EEG signal, such as relative to a stored (e.g., in the memory circuitry 118) baseline PSD EEG signal for that particular channel of a particular patient. Various techniques of acquiring and storing one or more suitable baseline PSD EEG signal templates are explained in more detail elsewhere herein. Techniques of selecting an appropriate baseline PSD EEG signal template from among multiple stored suitable baseline PSD EEG signal templates (e.g., acquired under different conditions, etc.) are also explained in more detail elsewhere herein. An average or other central tendency, at respective spectral bin frequencies, of multiple baseline PSD EEG signal templates acquired under similar conditions, can be determined, stored, and used as a baseline PSD EEG signal, as desired.

After selecting an appropriate monitored pre-processed baseline PSD EEG signal template for use in the baseline adjustment of a current PSD EEG signal, a baseline-adjusted monitored PSD EEG signal can be obtained, for example, by dividing (or subtracting or otherwise relatively adjusting) the monitored pre-processed PSD EEG signal by the selected stored baseline PSD EEG signal at individual spectral bin frequencies within the specified overall range of frequencies (e.g., within an overall range from 0.1 Hz or 1.0 Hz through 20 Hz or 30 Hz). The individual spectral bin frequencies for which such division is performed can involve corresponding individual spectral bin frequencies at a spectral resolution between 0.1 Hz to 1 Hz, spanning the overall specified frequency range, e.g., 0.1 Hz to 64 Hz.

Figure 4:
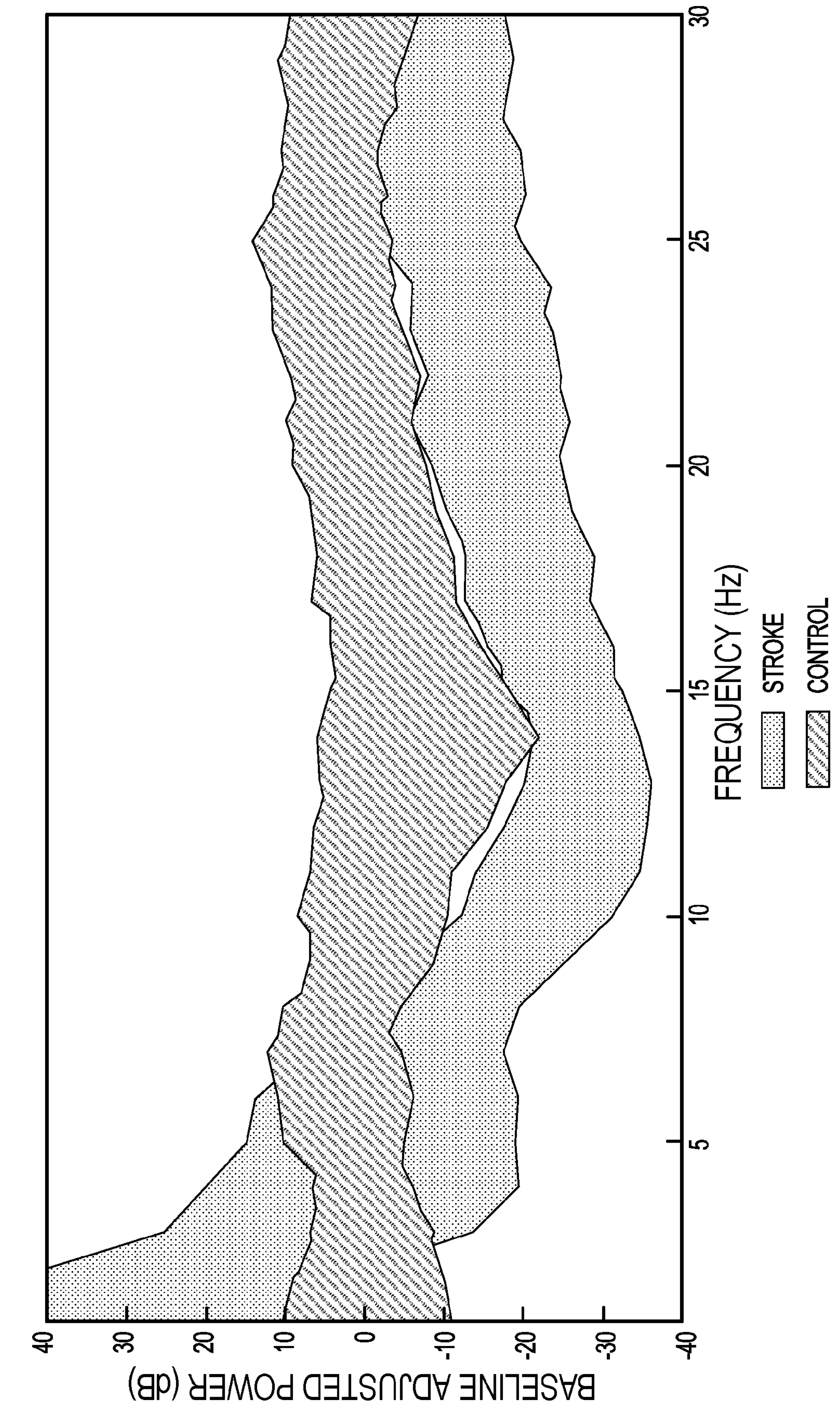
FIG. 4 shows an example of a baseline-adjusted PSD EEG signal spectral power (dB) vs. frequency (Hz) for a number of different pre-stroke control periods (blue) and a number of post-stroke periods.

Classifier circuitry 206 can include single or multiple channel inputs to receive the baseline-adjusted PSD EEG signal from the Baseline-Adjustment circuitry 204. The classifier circuitry 206 can apply one or more criteria to determine whether a relatively new or recent stroke condition has been detected, such as using the baseline-adjusted PSD EEG signal from the Baseline-Adjustment circuitry 204. For example, if a "temporal shift" in the PSD EEG signal over a specified frequency range (e.g., e.g., 0.1 Hz or 1.0 Hz through 20 Hz or 30 Hz) or a specified sub-range exceeds a specified amount, the classifier circuitry 206 can deem or declare a new or recent stroke condition to have occurred. Such a temporal shift can be determined in a number of different ways. One way of determining temporal shift is by determining a change spectral power amplitude from a corresponding baseline value of spectral power amplitude, at a specified one or more spectral bins, over a specified period of time. For example, a temporal dip (e.g., a decrease in spectral power amplitude over a specified period of time) in a mid-frequency sub-range of the specified overall frequency range can be indicative of a detected new or recent stroke condition, such as shown in FIG. 4. The classifier circuitry 206 can use the trained model 124 to detect the temporal dip, such as with the model 124 trained as explained elsewhere in this document. The classifier circuitry 206 can include an alert-blanking, alert-attenuation, or other alert-suppression module to at least one of blank, attenuate, or suppress generation of the stroke detection alert, such as in response to a migraine, post-migraine, seizure, post-seizure, post-ictal or other stroke mimic or other confounding condition. This can include training the same model 124 and including stroke mimic data as ground truth data representative of non-stroke occurrences, or it can include training a separate stroke mimic model that can be applied together with the stroke detection model 124, such as to at least one of blank, attenuate, or suppress generation of the stroke detection alert.

FIG. 4 shows an example of a baseline-adjusted PSD EEG signal spectral power (dB) vs. frequency (Hz) for a number of different pre-stroke control time window periods (blue) and a number of post-stroke time window periods. From FIG. 4, it can be observed that there is a temporal dip in the mid-frequency sub-range of the specified overall frequency range of 0 Hz to 30 Hz. By monitoring for and detecting this temporal mid-frequency sub-range temporal dip, such as using a trained learning model or other technique, a Stroke Detection alert can be generated, such as described herein. Although FIG. 4 has given a particular example of a temporal dip in the mid-frequency subrange of an overall specified frequency range, one or more other characteristics of a temporal shift in the baseline-adjusted PSD EEG signal can be indicative of stroke. For example, a temporal increase in a lower frequency sub-range of the specified overall frequency range can also be indicative of stroke. Therefore, it can be beneficial to use the trained learning model, trained with an appropriate training data set, for detecting one or more characteristics of a temporal shift in the baseline-adjusted PSD EEG signal.

In FIG. 2, if a temporal dip in a mid-frequency range of the specified frequency range is detected, such as using the trained learning model or other technique, an appropriate "Stroke Detected" classification can be declared by the classifier circuitry 206 such as for a particular channel, and such information can be communicated to the stroke alert generator 126, which, in turn, can communicate a Stroke Detected alert via the onboard or local auxiliary communications transceiver 128 and the mobile telephony communications network 132 (or other communications modality), such as to one or both of the alert recipient transceiver 130 or to the local/remote server local or remote server system 134. In an example in which baseline-adjusted PSD EEG signal data is streamed to a local or remote auxiliary computing device for analysis using the trained learning model, the alert can be generated at and communicated from the local or remote auxiliary computing device.

For performing baseline adjustment and classification, a baseline PSD EEG signal is first acquired and stored, such as by baseline acquisition and storage circuitry 203. Baseline acquisition and storage circuitry 203 can include inputs coupled to receive an output from Power Spectral Density PSD circuitry 202, such as to receive a current pre-processed monitored PSD EEG signal during a baseline acquisition mode. One or more appropriate segments of a pre-processed monitored PSD EEG signal from Power Spectral Density PSD circuitry 202 can be captured and stored in memory by baseline acquisition and storage circuitry 203 as corresponding baseline PSD EEG signal templates, which can then be selected, output, and provided to the Baseline-Adjustment circuitry 204 for performing baseline-adjustment.

During the baseline acquisition mode, the baseline acquisition and storage circuitry 203 can acquire and the memory circuitry 118 can store one or multiple non-stroke baseline PSD EEG signals, for example, such as which can be individually associated with different non-stroke sampled time periods, such as from the same channel of the same subject. The Baseline-Adjustment circuitry 204 can be configured to select a particular stored baseline PSD EEG signal from among several different available choices of non-stroke baseline PSD EEG signal templates.

One way to perform such selection of a stored non-stroke baseline PSD EEG signal can be based on a distance or correlation coefficient or other similarity characteristic between the particular stored non-stroke baseline PSD EEG signal and the monitored PSD EEG signal. For example, Mahalanobis distance, Minkowski distance, Euclidean distance, or other suitable distance metric between the particular non-stroke stored baseline PSD EEG signal and the monitored PSD EEG signal. In this way, a stored non-stroke baseline PSD EEG signal that most closely resembles current conditions can be used by the Baseline-Adjustment circuitry 204 for performing baseline adjustment. Choosing a stored non-stroke baseline PSD EEG signal that most closely resembles current conditions can help increase specificity of any resulting stroke detection alert that is generated, such as by using the trained learning model to detect a temporal shift in a current PSD EEG signal from the stored non-stroke baseline PSD EEG signal.

Additionally or alternatively, selecting a stored non-stroke baseline PSD EEG signal can utilize ancillary information about one or more conditions present during acquisition of the stored non-stroke baseline PSD EEG signal in the acquisition mode, and a comparison to information about whether any of those one or more conditions are present during an operating mode in which stroke monitoring and detection is being performed.

For example, the baseline acquisition and storage circuitry 203 and the Baseline-Adjustment circuitry 204 can include or be coupled to one or more sensors 205. For example, the one or more sensors 205 can include time-sensing circuitry such as clock circuitry. Such clock circuitry can provide time information, such as time-of-day, day-of-week, or date. Additionally or alternatively, such clock circuitry can provide a classification of time-of-day into daytime or nighttime. Such time information can be stored together with the stored non-stroke baseline PSD EEG signal during acquisition mode. During operating mode, when stroke monitoring and detection is being performed, a stored baseline PSD EEG signal template having a similar time-of-day characteristic or classification can be selected and used by Baseline-Adjustment circuitry 204 for performing baseline adjustment. Similarity between a current characteristic (e.g., time-of-day) being provided by the one or more sensors 205, and a sensor characteristic present during acquisition of a particular stored baseline PSD EEG signal during acquisition mode can be used as a sole selection criterion for selecting the particular stored baseline PSD EEG signal, or it can be used as a factor that can be weighted or otherwise considered together with one or more other factors for selecting the particular stored baseline PSD EEG signal, if desired.

The one or more sensors 205 can include an activity sensor, such as can include one or more of an accelerometer or a gyroscope to detect the subject's movement or physical activity, or an EMG sensor to detect the subject's muscle activity, or the like. Such activity information can be stored together with the stored non-stroke baseline PSD EEG signal during acquisition mode. During operating mode, when stroke monitoring and detection is being performed, a stored baseline PSD EEG signal template having a similar activity characteristic or classification can be selected and used by Baseline-Adjustment circuitry 204 for performing baseline adjustment. Similarity between a current characteristic (e.g., activity) being provided by the one or more sensors 205, and a sensor characteristic present during acquisition of a particular stored baseline PSD EEG signal during acquisition mode can be used as a sole selection criterion for selecting the particular stored baseline PSD EEG signal, or it can be used as a factor that can be weighted or otherwise considered together with one or more other factors for selecting the particular stored baseline PSD EEG signal, if desired.

The one or more sensors 205 can include a sleep sensor, such as can provide sleep information, such as a sleep status or sleep stage of the subject. Examples of sleep status or sleep stage can include, for example, awake, drowsy, REM sleep, as well as non-REM sleep (NREM) stage 1, NREM stage 2, NREM stage 3, or other sleep or wakefulness or level of arousal stage or state of the same subject, such as can be determined by a sleep sensor in the one or more sensors 205. The sleep sensor can be a standalone sleep sensor, or it can derive sleep status or sleep stage information based upon information received from one or more other sensors. For example, sleep information can be derived from Heart Rate Variability (HRV) information, which, in turn can be sensed from an electrocardiogram (ECG) sensor, an accelerometer providing a cardiac stroke signal, a gyro, or a photoplethysmography (PPG) sensor, or other sensor. The sleep sensor may monitor one or more physiological factors (e.g., heart rate variability (HRV), blood pressure, rapid-eye-movement (REM) sensor, or one or more EEG signals) such as to help determine the sleep status or sleep stage of the subject. Such information acquired with a PSD EEG signal during acquisition mode can be stored together with PSD EEG signals corresponding to different sleep status or sleep stage. During operation mode, in which stroke monitoring or detection is being performed, the current sleep status of the subject can be compared to the sleep status or sleep stage corresponding to the one or more stored baseline PSD EEG signal templates and used to select (either as a sole criterion, or as one factor in multi-factor selection criteria) an appropriate baseline PSD EEG signal template, such as one that matches the subject's current sleep status or sleep stage.

Co-morbidity information, confounding condition information, or other stroke-relevant information can also be communicated to the stroke monitor device 102, such as from user interface 136 or elsewhere, such as for use in either acquisition mode when acquiring one or more baseline PSD EEG templates, for use in operating mode when monitoring for a stroke, or for use in both acquisition and operating modes. Such information can be used for, among other things, selecting similar conditions during which an appropriate stored baseline PSD EEG template was acquired, during acquisition mode, for use together with presently-occurring conditions in an operating mode for stroke monitoring or detection. Examples of confounding conditions can include, among other things, a migraine, post-migraine, seizure, post-seizure, post-ictal or other stroke mimic or other confounding condition from the same subject or from a different subject.

Medication status (e.g., prescription, titration timing, or both) can also be useful stroke-relevant information communicated to the stroke monitor device 102, such as from user interface 136 or elsewhere can also be communicated to the stroke monitor device 102, such as from user interface 136 or elsewhere, such as for use in either acquisition mode when acquiring one or more baseline PSD EEG templates, for use in operating mode when monitoring for a stroke, or for use in both acquisition and operating modes. For example benzodiazepines can affect EEG signals and, therefore, can possibly impact the baseline PSD EEG templates or the current PSD EEG signals being monitored. More generally, medication prescription or titration information, or both, may be useful for selecting (or helping select) an appropriate baseline PSD EEG template for comparing a monitored PSD EEG signal for stroke monitoring and detection.

In addition or alternative to baseline PSD EEG template selection for baseline adjustment, any of (or any combination of) the medication information, confounding or comorbidity information, physiological sensor information, may also be used for adjusting one or more metrics used by the classifier circuitry 206 in classifying the monitored PSD EEG signal as detected stroke, with such metrics explained in further detail elsewhere herein.

The selected baseline PSD EEG template and the one or more stroke classification metrics used by the classifier circuitry 206 need not be static. For example, the particular baseline PSD EEG template or one or more stroke classification parameters or metrics, or both, can be changed, such as in response to a change in conditions or one or more triggering events. For example, a baseline adjustment triggering event may be triggered by information received from the one or more sensors 205. For example, the one or more sensors 205 can include one or more of an accelerometer, a gyroscope, a sleep sensor, a temperature sensor, a blood flow sensor, a blood oxygenation (SpO2) sensor, a tissue oxygenation (e.g., near infrared spectroscopy (NIRS)) sensor or other sensor including or ancillary to the one or more EEG skin electrodes, for example. For example, an accelerometer can provide information about the patient's activity level. In an example, the accelerometer can provide an indication of patient activity level, which can be combined with time-of-day or sleep status information, to select an appropriate baseline PSD EEG template, one or more stroke classification parameters or metrics, or both. A gyroscope can provide patient position information (e.g., standing, sitting, recumbent, prone, left lateral decubitus, right lateral decubitis, or the like), which can be used or combined with other information such as to select an appropriate baseline PSD EEG template, one or more stroke classification parameters or metrics, or any of these.

In addition or alternative to using triggering event information from the one or more sensors 205, from the user interface 136, or from elsewhere, to select a stored baseline PSD EEG signal, such triggering event information can be used to triggering updating (e.g., acquisition mode) of the baseline PSD EEG signal in response to such a triggering event. For example, after occurrence of a confirmed or other detected stroke or other neurological event, there can be a post-event shift in the PSD EEG signal. Therefore, to detect a subsequent stroke in the wake of such a stroke or other neurological event, it can be advantageous acquire a new post-event baseline PSD EEG signal, which can be used by Baseline-Adjustment circuitry 204 for baseline adjustment of the monitored PSD EEG signal, so that deviations from the post-event baseline PSD EEG signal can be used by the classifier circuitry 206 to monitor for a subsequent stroke event and alert accordingly.

Another example of a triggering event can include elapsing of an update clock timer, recognizing that any acquired baseline PSD EEG signal template may become less valid over time, making baseline PSD EEG signal template re-acquisition and updating desirable for continued accurate stroke monitoring and detection.

Another example of a triggering event can include encountering a sampled duration of the monitored PSD EEG signal deviating from the stored baseline PSD EEG signal by at least a specified amount (e.g., using one or more of the distance measurements described herein). While classifier circuitry 206 can be trained to determine whether such deviation is indicative of a detected stroke, there is also the possibility that a different nature of such deviation occurs—deviation in a manner that is not indicative of a detected stroke. Such deviation can be measured and, if it persists, can be used to trigger baseline PSD EEG signal template re-acquisition and updating, which can be desirable for continued accurate stroke monitoring and detection.

Another example of a triggering event can include or be based on receiving input from a physician or other caregiver, the subject patient, or other user input, such as can be provided via user interface 136. This can allow for a wide variety of non-stroke circumstances that may merit triggering template re-acquisition and updating, which can be desirable for continued accurate stroke monitoring and detection.

Figure 5:
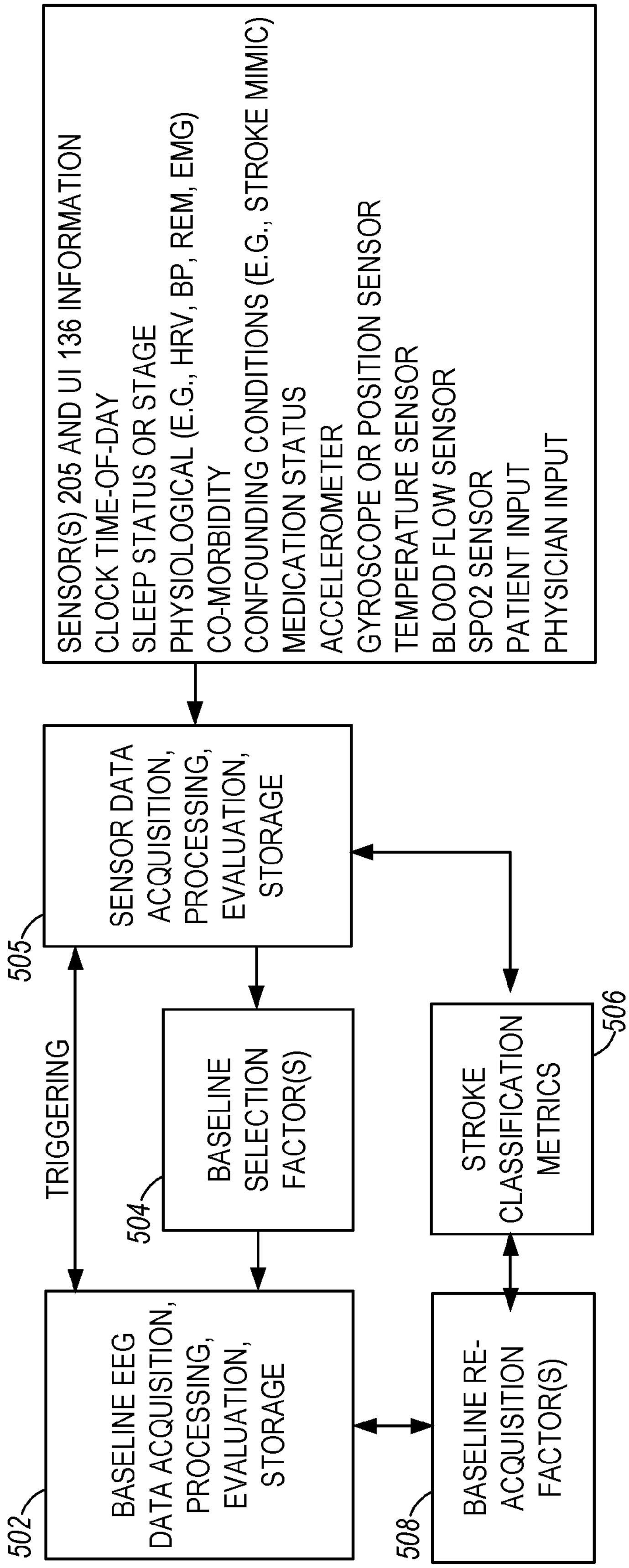
FIG. 5 is a block diagram of various interactions that can occur during EEG baseline acquisition, such as which can be triggered by sensor output status changes or other sensor output information or information received via the user interface.

FIG. 5 is a block diagram that recaps various interactions, such as explained above, that can occur during EEG baseline acquisition at 502, which can be triggered by sensor 205 output status changes or other sensor output information or information received via the user interface 136. The EEG baseline acquired data can be processed, evaluated, and stored, such as together at 505 with sensor data that is concurrently acquired, and which can also be processed, evaluated, and stored, such as in correspondence with the stored baseline data. During run-time monitoring for a stroke, the various sensors can be used at 504 as a factor for selecting an appropriate stored EEG baseline, or at 506 for selecting or modifying one or more stroke classification metrics, or at 508 as a factor for triggering baseline re-acquisition.

Figure 6:
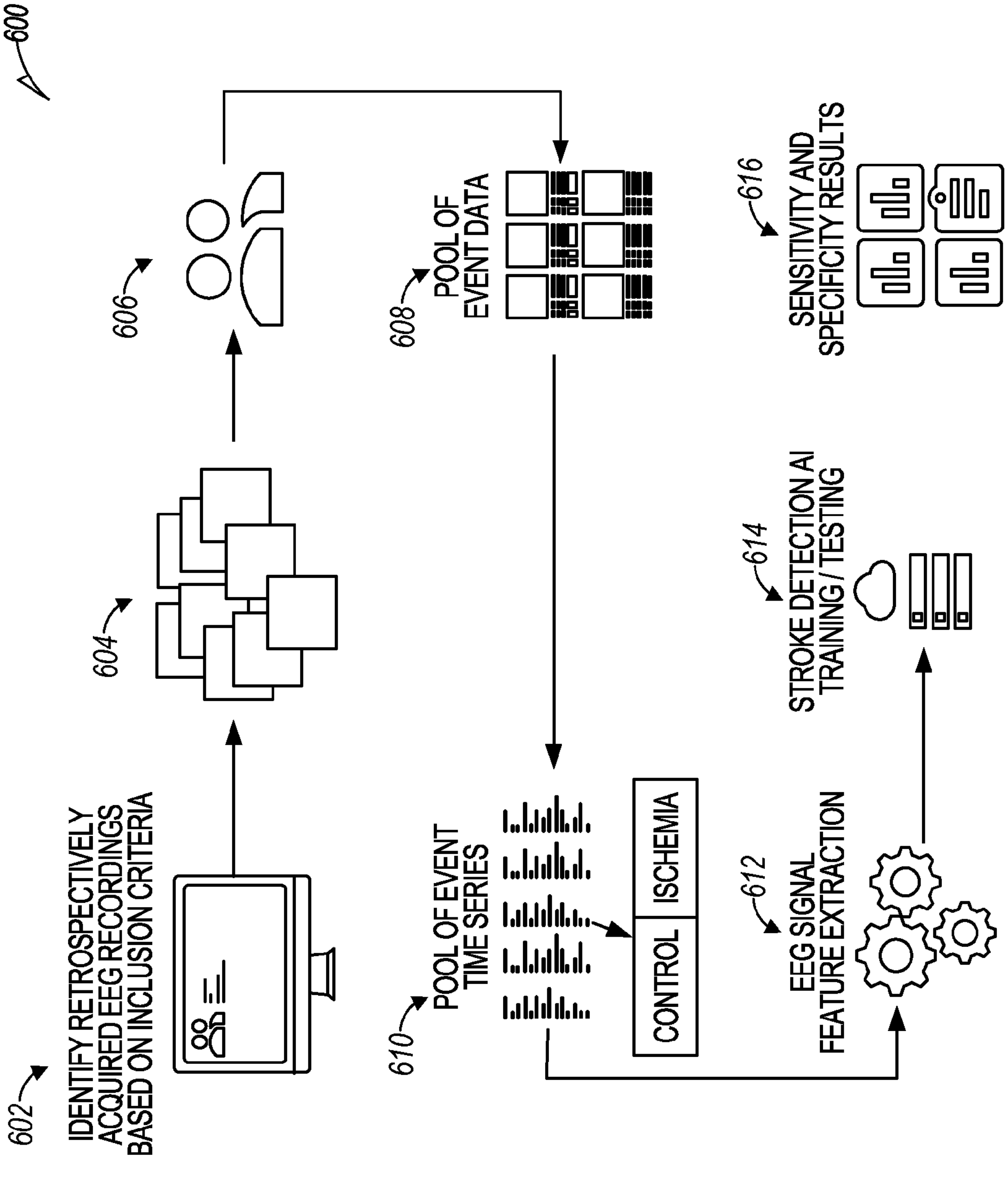
FIG. 6 is a flow chart illustrating generally portions of an example of a method of training and testing a learning model, such as for use of the trained learning model by classifier circuitry for performing stroke detection.

FIG. 6 is a flow chart illustrating generally portions of an example of a method 600 of training and testing the learning model 124, such as for use of the trained learning model 124 by the classifier circuitry 206 for performing Stroke Detection.

At 602, a training data set is developed. In an illustrative example, this included analyzing EEG time-series from patients exhibiting ischemia while undergoing surgery (IONM data). Patients sometimes experience ischemia because of the surgical manipulations involved in these procedures. IONM data can be used as a satisfactory source of EEG timeseries in which large vessel ischemia is occasionally captured in real-time. This can permit such data to be used as training set data for classification of onset of ischemia, as defined by one or more neurologists having additional training in neurophysiological monitoring.

At 602, in another example of developing a training data set, the process can include identifying non-surgical EEG time series (e.g., single electrode time domain tracings) where ischemic events have taken place. The time series can be extracted from a dedicated EEG database for further analysis. The dedicated EEG database may include data captured by the system described in the present disclosure or from one or more other data sources such as one or more of: surgical neuromonitoring recordings or intensive care unit (ICU) neuromonitoring recordings in which the ICU patients may have exhibited ischemic event data.

At 604, IONM (or non-surgery-related EEG) data is pooled, such as for use in generating a training data set for training the learning model 124.

At 606, the trained neurophysiology experts review the single electrode time domain tracings and any annotations and label events, including events representative of brain ischemia (e.g., intrinsic or induced). Such event labeling by the trained neurophysiologists can be performed in the time-domain (e.g., before being converted into PSD EEG signal data), such as where the trained neurophysiologists are more comfortable in assessing the single electrode time domain tracings than the PSD EEG signal data. Additionally or alternatively, such event labeling by appropriately-trained neurophysiologists can also be performed in the frequency-domain, either before or after baseline-adjusting.

At 608, the resulting event-labeled data can be pooled into a training data set for training the for training the learning model 124.

At 610, the pool of valid event time-series data can be generated, such as with neurophysiologist-determined event labels including "Control," representing pre-ischemia-episode portions of time-series data, and "Ischemia" representing ischemia-present episode portions of the time series data, which are deemed to be representative of stroke, for the purposes of training the learning model 124. Such labelled events can provide a representation of "ground truth" for training the learning model 124. Additionally or alternatively, one or more Generative Adversarial Networks (GANs) or similar techniques can be employed for generating or training the learning model 124.

At 612, EEG signal feature extraction can be performed. This can include signal processing, such as via the noise suppression lowpass or bandpass filter 112 or bandpass filter circuitry, such as described above, and de-noising, such as by using the artifact filter circuitry 110, described above, and other signal processing similar to that performed by the analog front end circuitry 108, described above. Such signal pre-processing can be performed in the analog domain, such as would be performed by the stroke device 102, or if the time domain data has already been digitized for storage, similar time-domain signal processing can be performed in the digital domain. In the digital domain, after any analog-to-digital conversion, the training set data can be transformed into the frequency domain and represented as PSD EEG data, and baseline-adjusted, such as explained above.

At 614, the learning model 124 can be trained for stroke detection using the training data set after processing according to the EEG signal feature extraction of 612. Such training of the learning model 124 can use one or more artificial intelligence (AI) or machine learning (ML) techniques, such as to recognize a temporal shift over time such as toward the mid-frequency dip in the baseline-adjusted PSD EEG signal, such as shown in FIG. 4. In an example, the training of the model 124 for Stroke Detection classification by the classifier circuitry 206 can include applying a Random Forest ensemble learning technique. A Random Forest classifier is a supervised machine learning technique that can combine multiple individual classification trees using bootstrapped samples and randomly selected features at each node to determine a split (i.e., whether data fall in one branch of the tree or the other). The classification output can result from a voting procedure among the different classification trees and can be interpreted as representing a certainty of the model as to whether a Detected Stroke onset is occurring.

More generally, training of the model 124 can include supervised learning (e.g., classification, regression), unsupervised learning (e.g., clustering, manifold learning, biclustering, covariance estimation, density estimation, neural networks) or reinforcement learning. Some illustrative examples of machine learning models can include Support Vector Machines (SVM), stochastic gradient descent, naive Bayes, feature selection, least squares analysis, partial least square analysis, regression models (e.g., linear, logistic, polynomial), multivariate regression (e.g., stepwise, multivariate curve regression, alternating least squares, nonlinear), in addition or as an alternative to the Random Forest technique described above.

At 614, after training, testing or actual use of the trained model 124 for stroke detection can be performed. For testing, cross-validation can be performed on the training data set using a Leave-One-Out LOO) approach. In such an example, at least one case's data can be excluded from the training data set. Hence, by not seeding the training set with the omitted case, the trained model 124 can be used to detect an event that it has never seen before, i.e., a new onset of stroke event.

At 616, from such training and testing, sensitivity and specificity results can be evaluated. The trained model 124 can be configured to output a Stroke Probability Metric, such as a value within a range of values extending between 0 and 1, inclusive, with a temporal shift (change over time) toward a higher value indicating a greater likelihood that an onset of stroke has been detected. The Stroke Probability Metric can be compared to a fixed or an adjustable specifiable threshold value—with a "persistence characteristic" that meets one or more criteria—to generate a Thresholded Stroke Probability Metric, such as with a binary value "1" of the Thresholded Stroke Probability Metric indicating that the Stroke Probability has exceeded the threshold value in a manner that meets the one or more persistence characteristic criteria, and with a binary value "0" otherwise. When the Stroke Probability Metric exceeds the threshold value for a specified amount of time or for a time duration that meets or exceeds a specified number of time windows or in a manner that otherwise meets the one or more persistence characteristic criteria, a Stroke Detection event can be declared, and an Stroke Detection alert can be generated or one or more further specificity-enhancing rules can be applied before generating and communicating such a Stroke Detection alert.

As mentioned, in comparing the Stroke Probability Metric to an adjustably specifiable threshold, one or more persistence characteristic criteria can be applied (e.g., conjunctively, disjunctively, or in a specified combination) in making the comparison of the Stroke Probability Metric to the specified threshold value. As an illustrative example of multiple persistence characteristic criteria that can be applied in making the comparison of the Stroke Probability Metric to the specified threshold value, a first persistence criterion can include having exceeded a specified first threshold value continuously for at least a continuous specified first period of time, without the Stroke Probability Metric dropping below the specified threshold value during the continuous specified first period of time. A second persistence criterion can include having exceeded a specified second threshold value for at least a specified second period of time, but with the second persistence criterion allowing the Stroke Probability Metric to drop down below the specified second threshold value during the specified second period of time, provided that during the specified second period of time, the Stroke Probability Metric has cumulatively remained above the specified second threshold value for at least a cumulative specified third period of time. For example, the first and second persistence criteria can be disjunctively applied, such that if either one of the first and second persistence criteria is met, a Threshold Stroke Probability Metric having a binary value of “1” is generated, indicating that a Stroke Detection event has occurred. In an illustrative example, the first and second threshold values, to which the Stroke Probability Metric is compared, can be specified to be equal to each other. In an illustrative example, the cumulative specified third period of time can be specified to be longer in duration than the continuous specified first period of time.

One or more additional or alternative persistence criteria can similarly be defined and conjunctively or disjunctively or otherwise applied. For example, a third criterion can include an integration of an area under a curve of the Stroke Probability Metric that exceeds a specified first integration amount for a cumulative specified fourth period of time can be defined and conjunctively or disjunctively applied with one or more of the other criteria. In an example, a fourth criterion can include an integration of an area under a curve of the Stroke Probability Metric that exceeds a specified first integration amount for a cumulative consecutive specified fifth period of time can be defined and conjunctively or disjunctively applied with one or more of the other criteria.

Note that the above training and testing was performed using single-channel EEG data. In practice, the stroke monitor device 102 can include or be coupled to multiple wearable skin electrodes 106 (e.g., 4 or more, 5 or more, or even a larger number of skin electrodes), thereby providing corresponding different channels of information that can be separately pre-processed (e.g., using an individual baseline particular to a patient and a particular electrode located on that patient, if desired) and evaluated by the trained model 124 to provide multiple channels of Stroke Probability Metrics over a series of time periods.

In this way, the classifier circuitry 206 can be configured to generate a time-series of Thresholded Stroke Probability Metrics for corresponding ones of the time window periods, using the trained model 124, to classify the temporal shift in the baseline-adjusted monitored PSD EEG signal, over the specified overall range of frequencies, such as on a per-channel basis, that can optionally be combined with a function such as “voting” or any other function to determine whether the Thresholded Stroke Probability Metrics of the plurality of channels should yield a Stroke Detected indication for generating an alert. In an illustrative example, if a Thresholded Stroke Probability Metric of any one channel indicates Stroke Detected, then a detected stroke can be declared and alerted, and if a Thresholded Stroke Probability Metric of multiple channels indicates Stroke Detected, such multiple-channel Stroke Detected information can be used to (1) provide a Detected Stroke Intensity or Magnitude indicator having a higher value for a higher number of the multiple channels, or (2) provide a Detected Stroke Location indicator based on the one or more locations of the electrodes associated with the corresponding channels indicating Stroke Detected.

Figure 7:
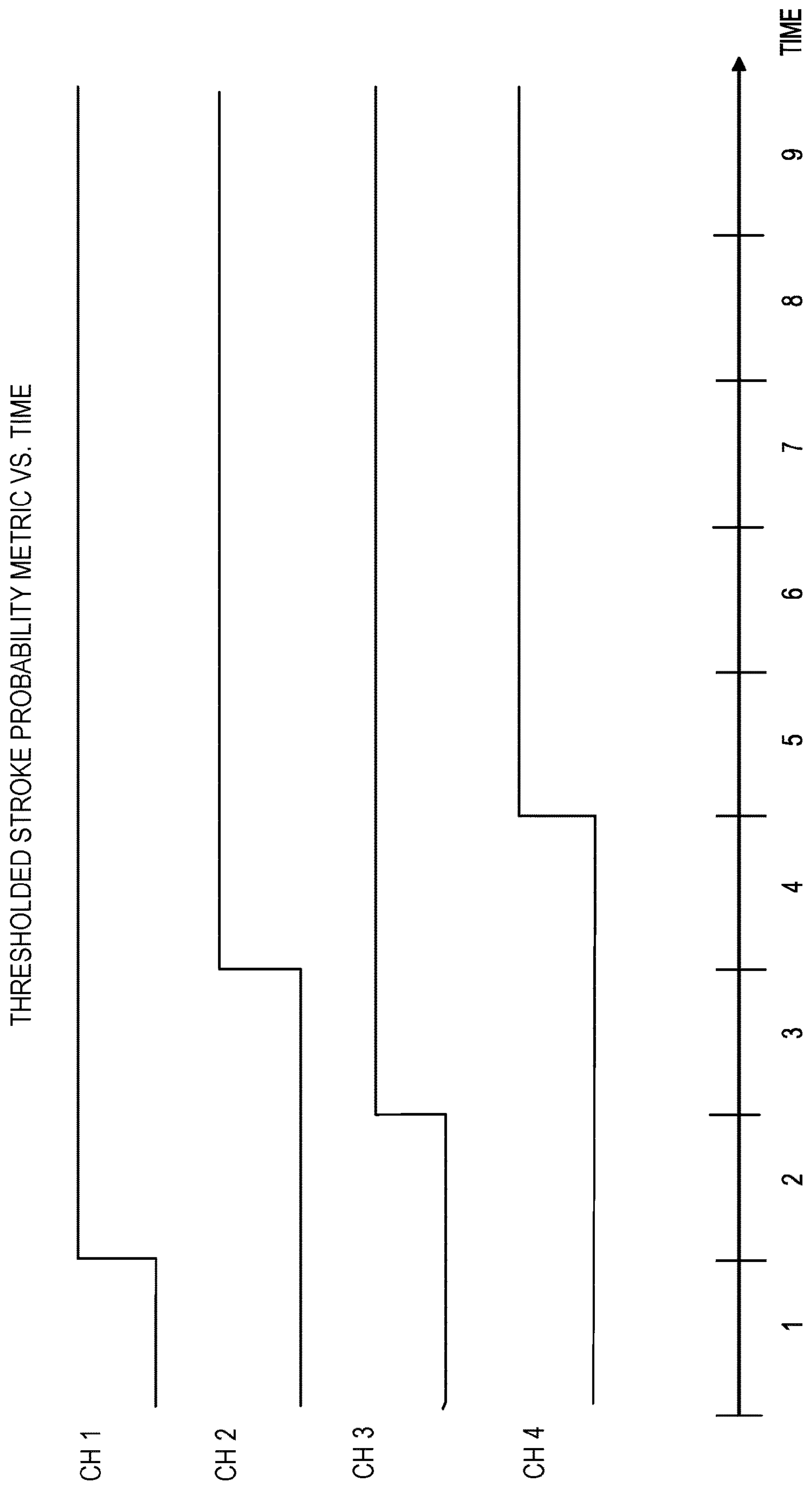
FIG. 7 shows an example of Stroke Probability Metric Comparison To Threshold vs. Time for an illustrative example showing four channels (Ch 1, Ch 2, Ch 3, Ch 4), although a different number of channels can be used.

FIG. 7 shows a conceptualized example of Stroke Probability Metric Comparison To Threshold (Thresholded Stroke Probability Metric) vs. Time for an illustrative example showing four channels (Ch 1, Ch 2, Ch 3, Ch 4, although a different number of channels can be used) in which the series of time-periods are shown to be non-overlapping. Such time-periods as shown in FIG. 7 can also be interchangeably referred to as “time units” or “time windows.” However, a partially overlapping series of time periods can be used, if desired. In this example of FIG. 7, a binary value indicative of the comparison of the Stroke Probability Metric to a corresponding threshold value (which can be the same threshold for all channels, or which can take on different threshold values for individual channels) is used, such as with one or more of the conjunctively or disjunctively applied persistence criteria, as explained above. For a particular channel, a binary value of “1” indicates “Stroke Detected” and a binary value of “0” indicates an absence of “Stroke Detected.” In an illustrative example, if a Thresholded Stroke Probability Metric of any one channel indicates Stroke Detected, then a detected stroke can be declared and alerted, e.g., at the beginning of time unit 2 for the conceptualized data in the example shown in FIG. 7.

In FIG. 7, if a rule for combining outputs from different channels is established, such that the alert indicating Detected Stroke is generated at least in part based on a plurality of consecutive (or non-consecutive but at least successive) indications of stroke probability metrics meeting at least one criterion. The criterion can be specified differently depending on whether consecutive or non-consecutive indications are specified as the rule. The particular specifications for the rule can depend upon, among other things, the setting in which the technique is employed, e.g., in a hospital setting vs. in an “at home” setting, or according to one or more other factors.

For example, for a SPM Comparison that is larger than a specified threshold (e.g., SPM>0.75 for SPM ranging from 0 to 1) in a manner that meets the one or more specified persistence characteristics, such as explained above, such that Thresholded SPM comparison=1 for at least a specified number (e.g., two) of channels for at least a specified number (e.g., three) successive time units then, in this example, a Stroke Detection can be declared at the beginning of time unit 6, based on Channels 1 and 3 meeting the criteria. Instead of using the binary value of the Thresholded SPM comparison to a threshold value, in another example, the actual SPM probability value (not a result from its comparison to a threshold) can be fed into a rule, such as for applying a combined threshold to a sum or product of the SPM probability values from the different channels. One or more other rules can be additionally or alternatively employed for generating a Stroke Detection indicator.

In FIG. 7, in an example, such multiple-channel Stroke Detected information (e.g., corresponding to the Thresholded Stroke Probability Metric, for a particular channel) can be used to provide a Detected Stroke Intensity indicator having a higher value for a higher number of the multiple channels. In an illustrative additive example, a Detected Stroke Intensity indicator can be “1” at the beginning of time unit 2, can be increased to “2” at the beginning of time unit 3, and can be increased to “3” at the beginning of time unit 4, and can be increased to “4” at the beginning of time unit “5”, thereby showing a progressive increase in Detected Stroke Intensity.

In FIG. 7, in an example, such multiple-channel Stroke Detected (or Thresholded Stroke Probability Metric) information can be used to provide a Detected Stroke Location indicator based on the one or more locations of the electrodes associated with the corresponding channels indicating Stroke Detected. For the conceptualized illustrative data shown in FIG. 7, the Stroke Detected (Thresholded Stroke Probability Metric=1) occurs first at an electrode location associated with Ch. 1, then at an electrode location associated with Ch. 3, then at an electrode location associated with Ch. 2, then at an electrode location associated with Ch. 4.

One or more rules can similarly be applied to such Detected Stroke Location indicator information. For example, a specified “atypical” distribution or progression in the Detected Stroke Location indicator information can be used to qualify or provide a confidence metric associated with the Stroke Detected indicator, such as to help improve specificity of the Stroke Detected alert generation.

FIGS. 8A-8K provide a conceptualized illustrative example of the present method of EEG signal-processing operation for stroke-detection. In this illustrative but non-limiting 4-channel EEG as an example, the four channels of EEG data, Ch. 1, Ch. 2, Ch. 3, and Ch. 4 can be generated from corresponding external electrodes worn on an external headband and respectively positioned in right lateral, right medial, left lateral, and left medial locations about the patient’s head such as to acquire EEG data at corresponding left side, right side, medial, or other brain locations.

Figures 8A, 8B, 8C, 8D:
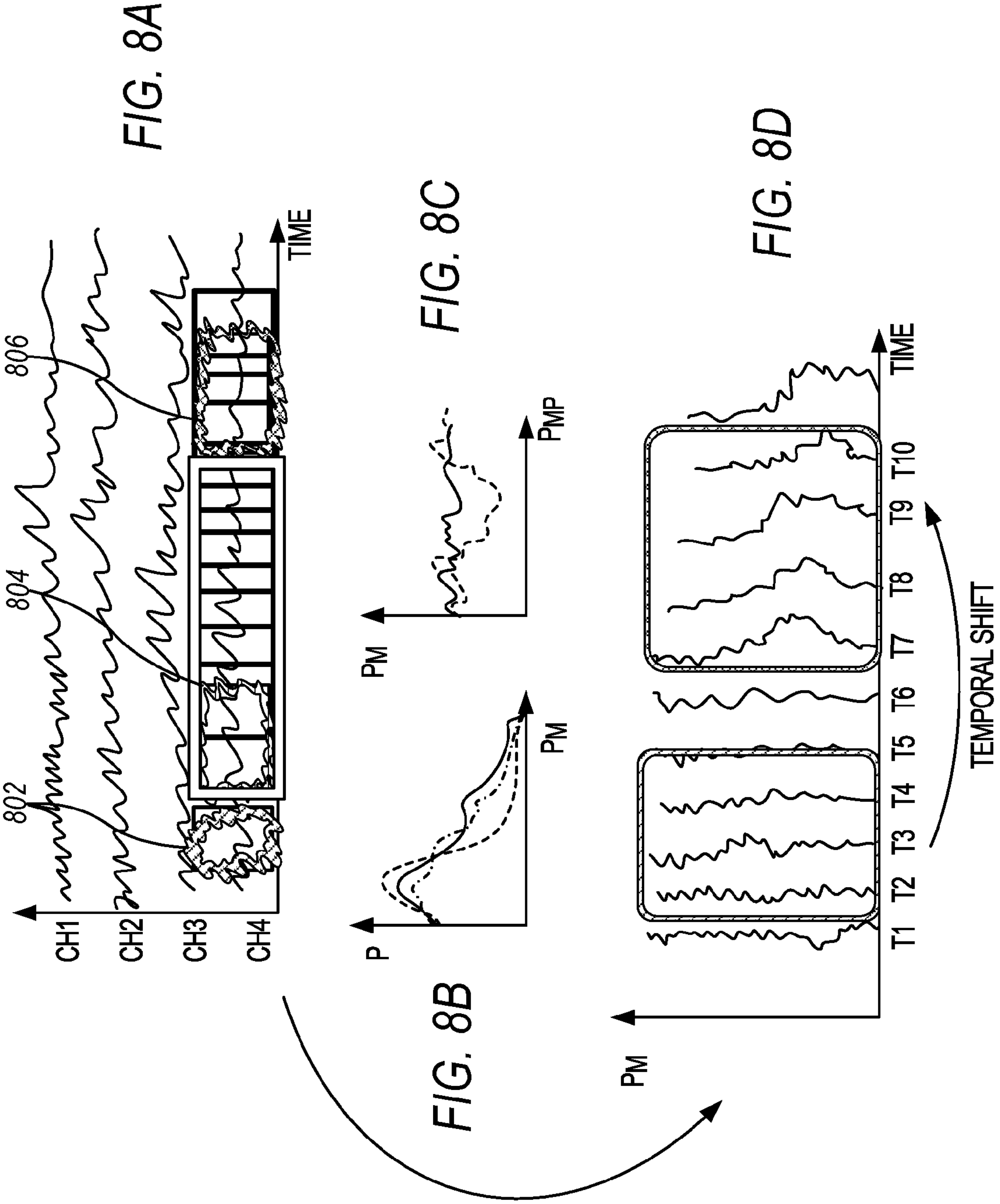
FIGS. 8A-8K provide a conceptualized illustrative example of the present method of EEG signal-processing operation for stroke-detection.

FIG. 8A shows the four channels of conceptualized EEG signal data vs. time, such as after signal pre-processing by the AFE circuitry 108, such as for filtering for artifact reduction, and digitization by the ADC 114. The left-most time window 802 illustrates a time-window used to capture a baseline EEG signal. Following the baseline-acquisition time window 802, to its right, FIG. 8A illustrates a next group of time-windows 804 used during acquisition of non-stroke EEG signals. Following this next group of time-windows 804 used during acquisition of non-stroke EEG signals, to its right, FIG. 8A illustrates a subsequent group of time windows 806 used during acquisition of EEG signal data progressively indicating stroke, as explained.

FIG. 8B shows a conceptualized example of Power Spectral Density (PSD) vs. frequency for baseline (green), non-stroke (blue), and stroke (orange) PSD examples over a corresponding time window 802, 804, 806.

FIG. 8C shows a conceptualized example of baseline-adjusted PSD vs. frequency for corresponding non-stroke (blue) and stroke time windows 804 and 806. In this example, the baseline adjusted PSD can be formed by dividing spectral bins of each of the non-stroke PSD and stroke PSD data by the corresponding spectral bins of the baseline data.

FIG. 8D shows a conceptualized example of baseline-adjusted PSDs (rotated counterclockwise) corresponding to various time windows $t_1, t_2, \ldots, t_n$. As can be seen from the conceptualized data of FIG. 8D, a temporal shift in the baseline-adjusted PSD data can be observed as the situation evolves over time to change from the non-stroke time windows 804 to the stroke time windows 806.

Figure 8E:
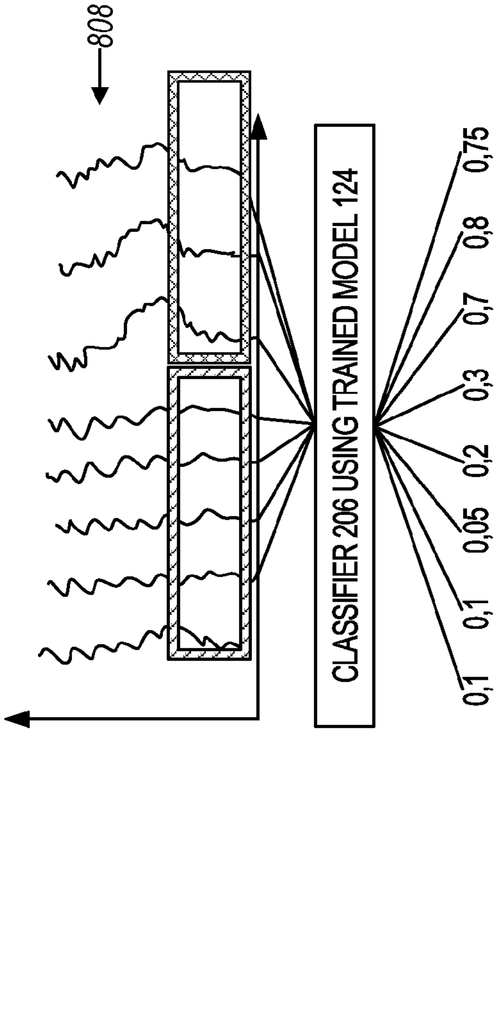

FIG. 8E shows a conceptualized example of a time-series of baseline-adjusted PSD curves being input into the classifier 206, which, using the trained model 124, outputs a corresponding time-series of Stroke Probability Metrics (SPMs) having a value between 0 and 1, each corresponding to a respective one of the time-windows of the input time-series of baseline-adjusted PSD curves. The value of the SPM increases away from 0 and toward 1 as the classifier 206 and trained model 124 deem a probability of stroke to be increasing.

Figure 8F:
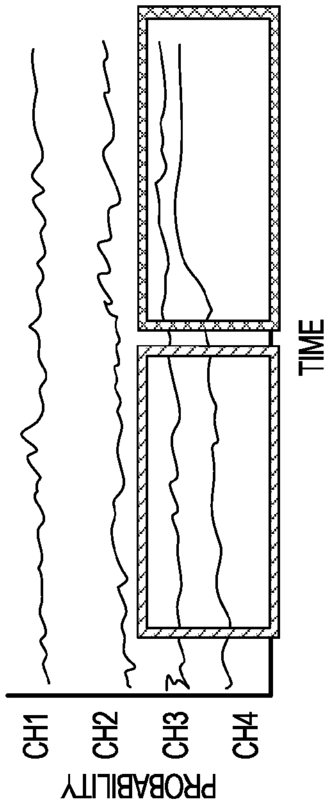

FIG. 8F shows a conceptualized example of SPM vs. time for each of the four EEG channels, Ch. 1, Ch. 2, Ch. 3, and Ch. 4. The SPM probability for a particular channel can be analyzed, such as by comparing the SPM to a threshold value and applying one or more persistence criteria, as explained herein.

Figure 8G:
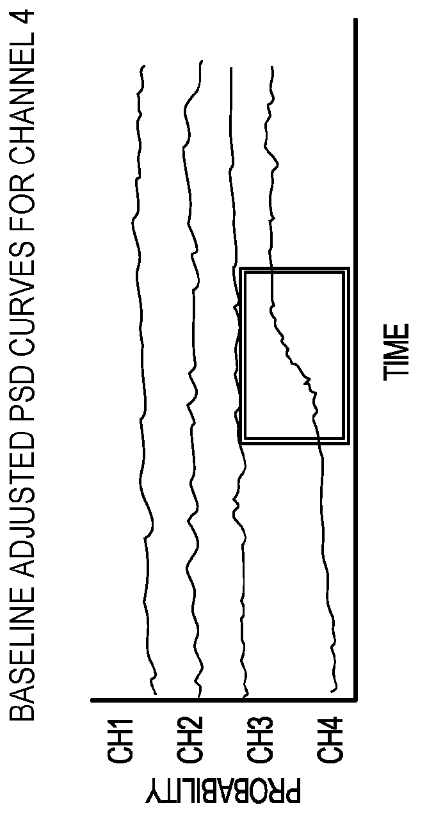

FIG. 8G shows a conceptualized example of 4 channels of SPM probability data vs. time, with an increase in SPM on Ch. 4 that can be analyzed such as by comparing the SPM to a threshold value and applying one or more persistence criteria, as explained herein, to generate a Threshold Stroke Probability Metric for Channel 4.

Figures 8H, 8I, 8J:
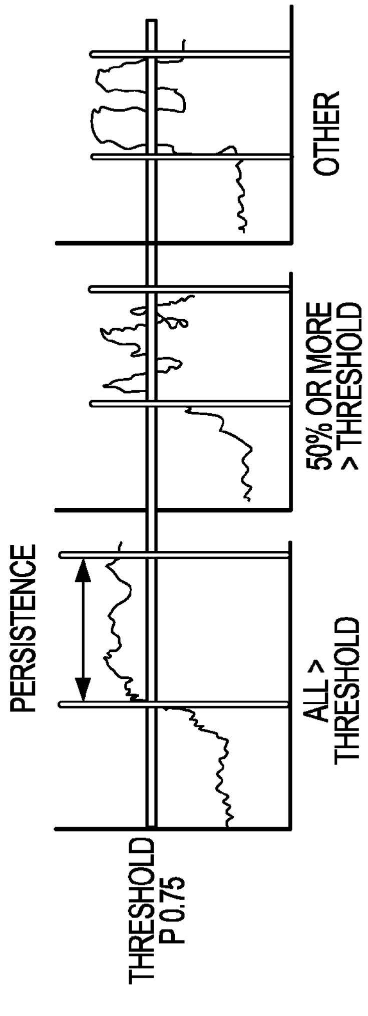

FIGS. 8H, 8I, and 8J show a conceptualized example of comparing an SPM fractional probability output by a particular channel to a specified threshold value (e.g., SPM>0.75) to generate a Thresholded SPM that is a binary “1” if one or more specified persistence criteria is also met, and “0” otherwise. FIGS. 8H, 8I, 8J illustrates a example in which if either:

(1) as shown in FIG. 8H, SPM>0.75 continuously (without dropping below the specified threshold) for at least a first specified time interval or duration (e.g., a specified first positive integer number of time windows 806); or (2) as shown in FIG. 8I, SPM>0.75 for more than a specified number or percentage (e.g., 50%) of the most recent time windows making up a second specified time duration (e.g., a specified second positive integer number of time windows 806, which can be different than the first specified positive number of time windows 805); or (3) as shown in FIG. 8J, SPM>0.75 and an area under the SPM curve exceeding the specified threshold exceeds a specified amount;

then if any one or more of the persistence criteria (1), (2), or (3) are met, a Thresholded SPM is set to a binary “1”, indicating Stroke Detected for that particular channel, unless optional additional specificity-enhancing criteria are to be applied.

Figure 8K:
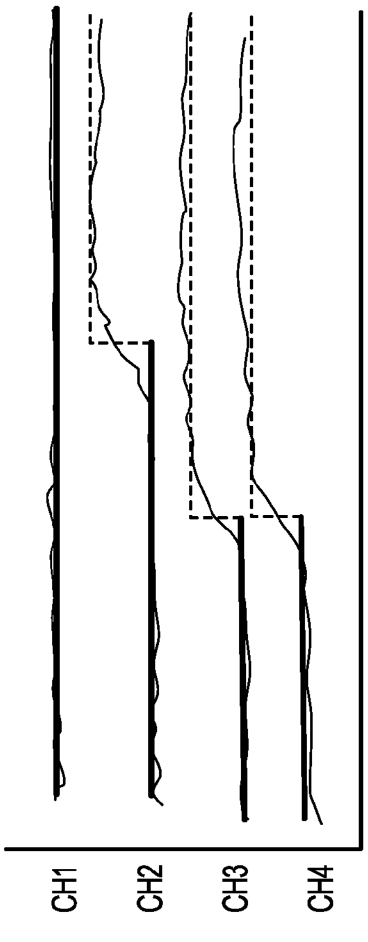

FIG. 8K illustrates a four-channel conceptualized example in which the Thresholded SPM (binary) is superimposed upon the SPM (fractional probability) and graphed against time, showing gradual increases in SPM first on Ch. 4, then Ch. 3, then Ch. 2, and corresponding changes in the binary value of the Thresholded SPM as the SPM meets the probability threshold value and at least one specified persistence criterion.

As described herein, the alert can be generated based on any one channel having a Thresholded SPM is set to a binary “1”, indicating Stroke Detected, or a “voting” or one or more other criteria or rules can optionally be applied to otherwise use the Thresholded SPM (or SPM) data for declaring Stroke Detected, Stroke Intensity, or the like, such as described herein.

For example, the classifier circuitry 206 can be configured to produce at least one of the alert indicating detected stroke, or an indication of certainty of the alert, based at least in part on a change between respective left-head and right-head temporal shifts in contralateral baseline-adjusted monitored PSD EEG signals, over a specified range of frequencies, such as on at least one of (1) a change between corresponding Left and Right channel baseline-adjusted PSD EEG signals; or (2) a relative temporal shift between contralateral Left and Right channel baseline-adjusted PSD EEG signals.

A numbered list of illustrative, non-limiting examples of various aspects of the present disclosure is presented below.

Example 1 can include an apparatus, device, method, system, article of manufacture, process, computer-readable medium with stored instructions, or the like, such as can include or use a wearable real-time stroke detector apparatus. The stroke detector can be configured to be coupled to one or more EEG skin electrodes. The one or more EEG skin electrodes can be located or locatable on a subject, such as for performing real-time or other stroke detection. The stroke detector apparatus can include signal processor circuitry. The signal processor circuitry can include power spectral density (PSD) circuitry. The PSD circuitry can be coupled to receive an acquired EEG signal. The EEG signal can be acquired, such as via a channel. The channel can be coupled to a skin electrode of the one or more EEG skin electrodes. The PSD circuitry can be configured to compute a monitored PSD EEG signal, such as can include using the acquired EEG signal. Baseline-adjustment circuitry can be coupled to the PSD circuitry, such as to receive the monitored PSD EEG signal. The baseline-adjustment circuitry can be coupled to memory circuitry, such as to receive a stored same-channel and same-subject baseline PSD EEG signal. The baseline-adjustment circuitry can be configured to form a baseline-adjusted monitored PSD EEG signal. This can include using the monitored PSD EEG signal and the baseline PSD EEG signal. Classifier circuitry can be coupled to the PSD circuitry, such as to receive the baseline-adjusted monitored PSD EEG signal. The classifier circuitry can include or use a trained model such as to classify a temporal shift in the baseline-adjusted monitored PSD EEG signal, such as over a specified range of frequencies, such as to produce an alert that can indicate Detected Stroke, such as based on the classified temporal shift as determined by the classifier circuitry using the trained model.

Example 2 can include or use, or can be combined with Example 1 such as to include or use baseline-adjustment circuitry that can be configured to periodically form the baseline-adjusted monitored PSD EEG signal over a series of time periods. The classifier circuitry can be configured to generate a time-series of stroke probability metrics, such as for corresponding ones of the time periods. The trained model can be configured and used to classify the temporal shift in the baseline-adjusted monitored PSD EEG signal, over the specified range of frequencies. The alert indicating Detected Stroke can be generated at least in part based on a plurality of successive indications of stroke probability metrics meeting at least one first criterion.

Example 3 can include or use, or can be combined with any one of Examples 1 or 2 such as to include or use the series of time periods including partially overlapping time periods.

Example 4 can include or use, or can be combined with any one of Examples 1 through 3, such that the alert indicating Detected Stroke can be generated at least in part based on a plurality of indications of consecutive stroke probability metrics meeting at least one second criterion.

Example 5 can include or use, or can be combined with any one of Examples 1 through 4, such that the alert indicating Detected Stroke can be generated at least in part based on a plurality of non-consecutive indications of stroke probability metrics meeting at least one third criterion.

Example 6 can include or use, or can be combined with any one of Examples 1 through 5, such that the baseline-adjustment circuitry can be configured to form the baseline-adjusted monitored PSD EEG signal, such as by dividing the monitored PSD EEG signal by the stored baseline PSD EEG signal at individual spectral frequencies within the specified range of frequencies.

Example 7 can include or use, or can be combined with any one of Examples 1 through 6, such that the memory circuitry can be configured to store multiple non-stroke baseline PSD EEG signals such as for selection by the baseline-adjustment circuitry such as to form the baseline-adjusted monitored PSD EEG signal such as using the monitored PSD EEG signal and the selected baseline PSD EEG signal.

Example 8 can include or use, or can be combined with any one of Examples 1 through 7, such that the memory circuitry can be configured to store multiple non-stroke baseline PSD EEG signals that can be individually associated with different non-stroke sampled time periods such as from the same channel of the same subject. The baseline-adjustment circuitry can be configured to select a particular stored baseline PSD EEG signal such as can be based on a distance or other similarity characteristic such as between the particular stored baseline PSD EEG signal and the monitored PSD EEG signal.

Example 9 can include or use, or can be combined with any one of Examples 1 through 8, such that the memory circuitry can be configured to store multiple non-stroke baseline PSD EEG signals such as which can be individually associated with at least one of:

(a) daytime or nighttime or other time-of-day characteristic;

(b) awake, drowsy, REM sleep, Stage 1 sleep, Stage 2 sleep, Stage 3 sleep, or Stage 4 sleep or other sleep or wakefulness or level of arousal stage or state of the same subject;

(c) medication prescription or usage status or characteristic of the same subject;

(d) a migraine, post-migraine, seizure, post-seizure, post-ictal or other stroke mimic or other confounding condition from the same subject or from a different subject; or (e) a physical activity or muscle activity status of the same subject.

Example 10 can include or use, or can be combined with any one of Examples 1 through 9, such that the baseline-adjustment circuitry can be configured to select a particular stored baseline PSD EEG signal such as based on at least in part on at least one sensor signal such as from at least one of an accelerometer, a gyroscope, a sleep sensor, a temperature sensor, a blood flow sensor, a blood oxygenation sensor, a tissue oxygenation sensor, or other sensor including or ancillary to the one or more EEG skin electrodes.

Example 11 can include or use, or can be combined with any one of Examples 1 through 10, such that the baseline-adjustment circuitry can be configured to update the stored baseline PSD EEG signal such as in response to or at a specified time interval after a trigger event. For example, the trigger event can include at least one of:

occurrence of a detected stroke or other indication of a neurological event;

elapsing of an update clock timer;

when a sampled duration of the PSD EEG signal deviates from the stored baseline PSD EEG signal by at least a specified amount; or a caregiver, patient, or other user input provided via a user or application interface.

Example 12 can include or use, or can be combined with any one of Examples 1 through 11, such that the classifier circuitry can include an alert-blanking, alert-attenuation, or other alert-suppression module, such as to at least one of blank, attenuate, or suppress generation of the alert in response to a migraine, post-migraine, seizure, post-seizure, post-ictal or other stroke mimic or other confounding condition.

Example 13 can include or use, or can be combined with any one of Examples 1 through 12, such that the model can be trained using baseline-adjusted PSD EEG signal data such as corresponding to physician or other human-based ground truth stroke determinations performed in the time domain using at least one of a raw EEG signal, an artifact-filtered EEG signal, or a noise-filtered artifact-filtered EEG signal from the same or a different subject undergoing an intrinsic or induced brain ischemia event.

Example 14 can include or use, or can be combined with any one of Examples 1 through 13, such that the classifier can be multi-channel corresponding to a number of different skin electrodes, and wherein the classifier can further be configured to indicate a stroke magnitude such as can be based at least in part on a number of channels respectively concurrently indicating detected stroke based on a corresponding plurality of consecutive stroke probability metrics meeting the at least one first criterion.

Example 15 can include or use, or can be combined with any one of Examples 1 through 14, such as can include or use artifact filter circuitry. The artifact filter circuitry can be configured to be coupled to the skin electrodes such as to receive a raw EEG signal from the skin electrodes and to remove or attenuate a non-EEG signal artifact comprising at least one of high electrode impedance, muscle activation, or eye movement, so as to produce an artifact-filtered EEG signal. Lowpass or bandpass filter circuitry can be coupled to the artifact filter circuitry such as to receive the artifact-filtered EEG signal. The filter circuitry can be configured to remove or attenuate high frequency noise, such as can include at least one of AC utility line noise or switching power supply line noise, so as to provide a noise-filtered artifact-filtered EEG signal as the acquired EEG signal for use by the PSD circuitry.

Example 16 can include or use, or can be combined with any one of Examples 1 through 15, such as can include the baseline-adjustment circuitry being configured to form a baseline-adjusted monitored PSD EEG signal such as by dividing or otherwise normalizing the monitored PSD EEG signal by the stored baseline PSD EEG signal at individual spectral frequencies within a specified range of frequencies.

Example 17 can include or use, or can be combined with any one of Examples 1 through 16, such as wherein the EEG signal includes Left and Right channels respectively corresponding to one or more skin electrodes located on one of a Left side of a brain of the subject or a Right side of a brain of the subject. The classifier circuitry can be configured to produce at least one of the alert indicating detected stroke, or an indication of certainty of the alert, based on at least one of (1) a change between contralateral Left and Right channel baseline-adjusted PSD EEG signals; or (2) a relative temporal shift between contralateral Left and Right channel baseline-adjusted PSD EEG signals.

Example 18 can include or use, or can be combined with any one of Examples 1 through 17, such as wherein the classifier can include multiple channels, such as with individual ones of the multiple channels respectively corresponding to a left-head and right-head skin electrodes. The classifier can be further configured to provide an alert certainty indication. The alert certainty indication can be based at least in part on a change between respective left-head and right-head temporal shifts in contralateral baseline-adjusted monitored PSD EEG signals, such as over a specified range of frequencies.

Example 19 can include or use, or can be combined with any one of Examples 1 through 18, such as to perform a method. The method can receiving an acquired EEG signal acquired via a channel coupled to a skin electrode of the one or more EEG skin electrodes. Using power spectral density (PSD) circuitry, the method can include computing a monitored PSD EEG signal using the acquired EEG signa. The method can also include receiving a stored same-channel and same-subject baseline PSD EEG signal. Using baseline-adjustment circuitry, the method can include forming a baseline-adjusted monitored PSD EEG signal using the monitored PSD EEG signal and the baseline PSD EEG signal. The method can also include classifying a temporal shift in the baseline-adjusted monitored PSD EEG signal, over a specified range of frequencies, such as using classifier circuitry. The classification can produce an alert. The alert can indicate Detected Stroke, such as can be based on the classified temporal shift such as determined by the classifier circuitry such as using the trained model.

Example 20 can include or use, or can be combined with any one of Examples 1 through 19, such as can include, using the baseline-adjustment circuitry, periodically forming the baseline-adjusted monitored PSD EEG signal over a series of time periods. The method can further include generating a time-series of stroke probability metrics, using the classifier circuitry, for corresponding ones of the time periods using the trained model to classify the temporal shift in the baseline-adjusted monitored PSD EEG signal, over the specified range of frequencies. An alert can be generated, such as indicating Detected Stroke, such as can be at least in part based on a plurality of successive indications of stroke probability metrics meeting at least one first criterion.

Example 21 can include or use, or can be combined with any one of Examples 1 through 20, such as can include or use forming the baseline-adjusted monitored PSD EEG signal such as by dividing the monitored PSD EEG signal by the stored baseline PSD EEG signal at individual spectral frequencies within the specified range of frequencies.

Example 22 can include or use, or can be combined with any one of Examples 1 through 21, to include or use a computer readable medium including stored instructions for performing the method of any one of Examples 1-21.

The above description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B"

includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A wearable real-time stroke detector apparatus, configured to be coupled to one or more EEG skin electrodes located on a subject for performing real-time stroke detection, the stroke detector apparatus comprising:

signal processor circuitry, comprising:

power spectral density (PSD) circuitry, coupled to receive an acquired EEG signal acquired via a channel coupled to a skin electrode of the one or more EEG skin electrodes, the PSD circuitry configured to convert the acquired EEG signal from a time-domain signal to a frequency-domain signal to compute a monitored PSD EEG signal representing a monitored power spectral density across an entire spectral range of frequencies from 1.0 Hz through 20 Hz using the converted acquired EEG signal;

baseline-adjustment circuitry, coupled to the PSD circuitry to receive a baseline of the monitored PSD EEG signal representing a baseline power spectral density across the entire spectral range of frequencies from 1.0 Hz through 20 Hz, and including or in combination with memory circuitry to receive a stored same-channel and same-subject baseline PSD EEG signal across the entire spectral range of frequencies from 1.0 Hz through 20 Hz, and to form a baseline-adjusted monitored PSD EEG signal across the entire spectral range of frequencies from 1.0 Hz through 20 Hz using the monitored PSD EEG signal and the baseline PSD EEG signal, wherein the memory circuitry is configured to store multiple non-stroke baseline PSD EEG signals across the entire spectral range of frequencies from 1.0 Hz through 20 Hz for selection by the baseline-adjustment circuitry to form the baseline-adjusted monitored PSD EEG signal across the entire spectral range of frequencies from 1.0 Hz through 20 Hz using the monitored PSD EEG signal and the selected baseline PSD EEG signal; and classifier circuitry, coupled to the PSD circuitry to receive the baseline-adjusted monitored PSD EEG signal, the classifier circuitry using the baseline-adjusted monitored PSD EEG signal and a trained model to classify a temporal shift across the entire spectral range of frequencies from 1.0 Hz through 20 Hz in the baseline-adjusted monitored PSD EEG signal to detect an elevation in a lower frequency portion of the entire spectral range and a depression in a higher frequency portion of the entire spectral range to produce a real-time detection indicating Detected Stroke based on the classified temporal shift as determined by the classifier circuitry using the trained model and, in response to the real-time detection, outputting an alert generated by the classifier circuitry indicating Detected Stroke to at least one of an alert recipient transceiver, a local or remote server, or a user interface device.

2. The stroke detector apparatus of claim 1, wherein:

the baseline-adjustment circuitry is configured to periodically form the baseline-adjusted monitored PSD EEG signal across the entire spectral range of frequencies from 1.0 Hz through 20 Hz over a series of time periods;

the classifier circuitry is configured to generate a time-series of stroke probability metrics for each respective one of multiple channels respectively corresponding to different EEG electrodes for corresponding ones of the time periods using the trained model to classify the temporal shift in the baseline-adjusted monitored PSD EEG signal, over the entire spectral range of frequencies from 1.0 Hz through 20 Hz; and wherein the alert indicating Detected Stroke is generated by the classifier circuitry at least in part based on a voting function applied to a specified number of respective ones of the multiple channels' respective stroke probability metrics meeting at least one corresponding threshold value criterion to which the stroke probability metric is compared.

3. The stroke detector apparatus of claim 2, wherein the classifier circuitry is configured to generate the alert indicating Detected Stroke based on a plurality of indications of the specified number of respective ones of the multiple channels' stroke probability metrics meeting at least one corresponding threshold value criterion, wherein the at least one corresponding threshold value criterion includes a first threshold value, to which the stroke probability metric is compared, for consecutive time periods for a particular channel and a different second threshold value, to which the stroke probability metric is compared, for non-consecutive time periods for the particular channel.

4. The stroke detector apparatus of claim 2, wherein the alert indicating Detected Stroke is generated at least in part based on a plurality of indications of consecutive stroke probability metrics meeting at least one second criterion comprising a second threshold value criterion that is specific to an occurrence of a specified number of consecutive time intervals.

5. The stroke detector apparatus of claim 2, wherein the alert indicating Detected Stroke is generated at least in part based on a plurality of non-consecutive indications of stroke probability metrics meeting at least one third criterion comprising a third threshold value criterion that is specific to an occurrence of a specified number of non-consecutive time intervals.

6. The stroke detector apparatus of claim 1, wherein the baseline-adjustment circuitry is configured to form the baseline-adjusted monitored PSD EEG signal across the entire spectral range of frequencies from 1.0 Hz through 20 Hz by dividing the monitored PSD EEG signal across the entire spectral range of frequencies from 1.0 Hz through 20 Hz by the stored baseline PSD EEG signal across the entire spectral range of frequencies from 1.0 Hz through 20 Hz at individual spectral frequencies across the entire spectral range of frequencies from 1.0 Hz through 20 Hz within the entire spectral range of frequencies from 1.0 Hz through 20 Hz.

7. The stroke detector apparatus of claim 1, wherein the memory circuitry is configured to store multiple non-stroke baseline PSD EEG signals having an entire spectral frequency range from 1.0 Hz through 20 Hz and individually associated with different non-stroke sampled time periods from a same channel of a same subject, and wherein the baseline-adjustment circuitry is configured to select a particular stored baseline PSD EEG signal based on a similarity characteristic determined over the entire spectral range of frequencies from 1.0 Hz through 20 Hz between the particular stored baseline PSD EEG signal and the monitored PSD EEG signal.

8. The stroke detector apparatus of claim 1, wherein the memory circuitry is configured to store multiple non-stroke baseline PSD EEG signals across the entire spectral range of frequencies from 1.0 Hz through 20 Hz individually stored in association with at least one of:

(a) time-of-day characteristic;

(b) a sleep or wakefulness or level of arousal stage or state of the subject, the stage or state including at least one of awake, drowsy, REM sleep, Stage 1 sleep, Stage 2 sleep, Stage 3 sleep, or Stage 4 sleep;

(c) medication prescription or usage status or characteristic of the subject;

(d) a migraine, post-migraine, seizure, post-seizure, post-ictal or stroke mimic confounding condition from the subject or from a different subject; or (e) a physical activity or muscle activity status of the subject obtained via at least one of an accelerometer, gyroscope, or EMG sensor.

9. The stroke detector apparatus of claim 1, wherein the baseline-adjustment circuitry is configured to select a particular stored baseline PSD EEG signal having the entire spectral range of frequencies from 1.0 Hz through 20 Hz based at least in part on at least one sensor signal from at least one of an accelerometer, a gyroscope, a sleep sensor, a temperature sensor, a blood flow sensor, a blood oxygenation sensor, a tissue oxygenation sensor, or sensor including the one or more EEG skin electrodes.

10. The stroke detector apparatus of claim 1, wherein the baseline-adjustment circuitry is configured to update the stored baseline PSD EEG signal across the entire spectral range of frequencies from 1.0 Hz through 20 Hz in response to or at a specified time interval after a trigger event, wherein the trigger event includes at least one of:

occurrence of a detected stroke;

or when a sampled duration of the PSD EEG signal deviates from the stored baseline PSD EEG signal by at least a specified amount.

11. The stroke detector apparatus of claim 1, wherein the classifier circuitry is configured to receive, via a user interface information indicating presence of a migraine, post-migraine, seizure, post-seizure, post-ictal or stroke mimic confounding condition and to automatically adjust at least one stroke classification metric of the classifier in response thereto.

12. The stroke detector apparatus of claim 1, wherein the model is trained using baseline-adjusted PSD EEG signal data across the entire spectral range of frequencies from 1.0 Hz through 20 Hz corresponding to ground truth stroke determinations performed in a time domain using at least one of a raw EEG signal, an artifact-filtered EEG signal, or a noise-filtered artifact-filtered EEG signal from a same or a different subject undergoing an intrinsic or induced brain ischemia event.

13. The stroke detector apparatus of claim 2, wherein the classifier is multi-channel corresponding to a number of different skin electrodes, and wherein the classifier is further configured to indicate a stroke magnitude based at least in part on a specified plurality of channels respectively concurrently indicating detected stroke based on a corresponding plurality of consecutive stroke probability metrics of the specified plurality of channels meeting the at least one threshold value criterion.

14. The stroke detector apparatus of claim 1, further comprising:

artifact filter circuitry, configured to be coupled to the skin electrodes to receive a raw EEG signal from the skin electrodes and to remove or attenuate a non-EEG signal artifact comprising at least one of high electrode impedance, EMG sensor indicated muscle activation, or eye movement, so as to produce an artifact-filtered EEG signal.

15. The stroke detector apparatus of claim 1 wherein the baseline-adjustment circuitry is configured to form a baseline-adjusted monitored PSD EEG signal across the entire spectral range of frequencies from 1.0 Hz through 20 Hz by normalizing the monitored PSD EEG signal across the entire spectral range of frequencies from 1.0 Hz through 20 Hz by the stored baseline PSD EEG signal across the entire spectral range of frequencies from 1.0 Hz through 20 Hz at individual spectral frequencies within a specified range of frequencies across the entire spectral range of frequencies from 1.0 Hz through 20 Hz.

16. The stroke detector apparatus of claim 1, wherein the EEG signal includes Left and Right channels respectively corresponding to one or more skin electrodes located on one of a Left side of a brain of the subject or a Right side of a brain of the subject, and wherein the classifier circuitry is configured to produce at least one of the alert indicating detected stroke, or an indication of certainty of the alert, based on at least one of (1) a change between contralateral Left and Right channel baseline-adjusted PSD EEG signals determined across the entire spectral range of frequencies from 1.0 Hz through 20 Hz; or (2) a relative temporal shift between contralateral Left and Right channel baseline-adjusted PSD EEG signals determined across the entire spectral range of frequencies from 1.0 Hz through 20 Hz.

17. The stroke detector apparatus of claim 1, wherein the classifier is multi-channel corresponding to left-head and right-head skin electrodes, and wherein the classifier is further configured to provide an alert certainty indication based at least in part on a change between respective left-head and right-head temporal shifts in contralateral baseline-adjusted monitored PSD EEG signals, over a specified range of frequencies that include an entire spectral range of frequencies from 1.0 Hz through 20 Hz.

18. A method of stroke detection, the method comprising:

using a wearable real-time stroke detector apparatus, configured to be coupled to one or more EEG skin electrodes located on a subject for performing real-time stroke detection, the stroke detector apparatus comprising: signal processor circuitry, comprising: power spectral density (PSD) circuitry, coupled to receive an acquired EEG signal acquired via a channel coupled to a skin electrode of the one or more EEG skin electrodes, the PSD circuitry configured to convert the acquired EEG signal from a time-domain signal to a frequency-domain signal and to compute a monitored PSD EEG signal representing a monitored power spectral density across an entire spectral range of frequencies from 1.0 Hz through 20 Hz using the converted acquired EEG signal; baseline-adjustment circuitry, coupled to the PSD circuitry to receive a baseline of the monitored PSD EEG signal representing a baseline power spectral density across the entire spectral range of frequencies from 1.0 Hz through 20 Hz, and including or in combination with memory circuitry to receive a stored same-channel and same-subject baseline PSD EEG signal across the entire spectral range of frequencies from 1.0 Hz through 20 Hz, and to form a baseline-adjusted monitored PSD EEG signal across the entire spectral range of frequencies from 1.0 Hz through 20 Hz using the monitored PSD EEG signal and the baseline PSD EEG signal, wherein the memory circuitry is configured to store multiple non-stroke baseline PSD EEG signals across the entire spectral range of frequencies from 1.0 Hz through 20 Hz for selection by the baseline-adjustment circuitry to form the baseline-adjusted monitored PSD EEG signal using the monitored PSD EEG signal and the selected baseline PSD EEG signal; and classifier circuitry, coupled to the PSD circuitry to receive the baseline-adjusted monitored PSD EEG signal, the classifier circuitry using the baseline-adjusted monitored PSD EEG signal and a trained model to classify a temporal shift across the entire spectral range of frequencies from 1.0 Hz through 20 Hz in the baseline-adjusted monitored PSD EEG signal to detect an elevation in a lower frequency portion of the entire spectral range and a depression in a higher frequency portion of the entire spectral range to produce a real-time detection indicating Detected Stroke based on the classified temporal shift as determined by the classifier circuitry using the trained model, the method further comprising:

receiving an acquired EEG signal acquired via a channel coupled to a skin electrode of the one or more EEG skin electrodes and, using the power spectral density (PSD) circuitry, converting the acquired EEG signal from a time-domain signal to a frequency-domain signal for computing a monitored PSD EEG signal representing a monitored power spectral density across an entire spectral range of frequencies from 1.0 Hz through 20 Hz using the converted acquired EEG signal;

selecting, using the baseline-adjustment circuitry, a selected baseline PSD EEG signal from stored multiple non-stroke baseline PSD EEG signals;

receiving a stored same-channel and same-subject baseline PSD EEG signal, and, using the baseline-adjustment circuitry, forming a baseline-adjusted monitored PSD EEG signal across the entire spectral range of frequencies from 1.0 Hz through 20 Hz using the monitored PSD EEG signal and the selected baseline PSD EEG signal; and classifying a temporal shift across the entire spectral range of frequencies from 1.0 Hz through 20 Hz in the baseline-adjusted monitored PSD EEG signal, using the classifier circuitry, to produce a real-time detection indicating Detected Stroke based on the classified temporal shift as determined by the classifier circuitry using the trained model and, in response to the real-time detection, outputting an alert generated by the classifier circuitry indicating Detected Stroke to at least one of an alert recipient transceiver, a local or remote server, or a user interface device.

19. The method of claim 18, comprising:

using the baseline-adjustment circuitry, periodically forming the baseline-adjusted monitored PSD EEG signal across the entire spectral range of frequencies from 1.0 Hz through 20 Hz over a series of time periods;

generating a time-series of stroke probability metrics, using the classifier circuitry, for corresponding ones of the time periods using the trained model to classify the temporal shift in the baseline-adjusted monitored PSD EEG signal, over the entire spectral range of frequencies from 1.0 Hz through 20 Hz; and generating the alert indicating Detected Stroke at least in part based on a plurality of successive indications of stroke probability metrics meeting at least one first criterion.

20. The method of claim 18 comprising forming the baseline-adjusted monitored PSD EEG signal across the entire spectral range of frequencies between 1.0 Hz and 20 Hz by dividing the monitored PSD EEG signal across the entire spectral range of frequencies from 1.0 Hz through 20 Hz by the selected baseline PSD EEG signal across the entire spectral range of frequencies from 1.0 Hz through 20 Hz at individual spectral frequencies across the entire spectral range of frequencies from 1.0 Hz through 20 Hz within the entire spectral range of frequencies from 1.0 Hz through 20 Hz.

21. A tangible physical computer readable medium including stored instructions for instructing signal processor circuitry for performing a method of stroke detection using a wearable real-time stroke detector apparatus, configured to be coupled to one or more EEG skin electrodes located on a subject for performing real-time stroke detection, the stroke detector apparatus comprising: the signal processor circuitry, comprising: power spectral density (PSD) circuitry, coupled to receive an acquired EEG signal acquired via a channel coupled to a skin electrode of the one or more EEG skin electrodes, the PSD circuitry configured to convert the acquired EEG signal from a time-domain signal to a frequency-domain signal and to compute a monitored PSD EEG signal representing a monitored power spectral density across an entire spectral range of frequencies from 1.0 Hz through 20 Hz using the converted acquired EEG signal; baseline-adjustment circuitry, coupled to the PSD circuitry to receive a baseline of the monitored PSD EEG signal, and coupled to memory circuitry to receive a stored same-channel and same-subject baseline PSD EEG signal representing a baseline power spectral density across the entire spectral range of frequencies from 1.0 Hz through 20 Hz, and to form a baseline-adjusted monitored PSD EEG signal across the entire spectral range of frequencies from 1.0 Hz through 20 Hz using the monitored PSD EEG signal and the baseline PSD EEG signal, wherein the memory circuitry is configured to store multiple non-stroke baseline PSD EEG signals across the entire spectral range of frequencies from 1.0 Hz through 20 Hz for selection by the baseline-adjustment circuitry to form the baseline-adjusted monitored PSD EEG signal using the monitored PSD EEG signal and the selected baseline PSD EEG signal; and classifier circuitry, coupled to the PSD circuitry to receive the baseline-adjusted monitored PSD EEG signal, the classifier circuitry using the baseline-adjusted monitored PSD EEG signal and a trained model to classify a temporal shift across the entire spectral range of frequencies from 1.0 Hz through 20 Hz in the baseline-adjusted monitored PSD EEG signal, to produce an alert indicating Detected Stroke based on the classified temporal shift as determined by the classifier circuitry using the trained model, the method comprising:

receiving an acquired EEG signal acquired via a channel coupled to a skin electrode of the one or more EEG skin electrodes and, using the power spectral density (PSD) circuitry, converting the acquired EEG signal from a time-domain signal to a frequency-domain signal for computing a monitored PSD EEG signal representing a monitored power spectral density across an entire spectral range of frequencies from 1.0 Hz through 20 Hz using the converted acquired EEG signal;

selecting, using the baseline-adjustment circuitry, a selected baseline PSD EEG signal from stored multiple non-stroke baseline PSD EEG signals;

receiving a stored same-channel and same-subject baseline PSD EEG signal, and, using the baseline-adjustment circuitry, forming a baseline-adjusted monitored PSD EEG signal across the entire spectral range of frequencies from 1.0 Hz through 20 Hz using the monitored PSD EEG signal and the selected baseline PSD EEG signal; and classifying a temporal shift in the baseline-adjusted monitored PSD EEG signal, across the entire spectral range of frequencies from 1.0 Hz through 20 Hz, using the classifier circuitry to detect an elevation in a lower frequency portion of the entire spectral range and a depression in a higher frequency portion of the entire spectral range to produce a real-time detection indicating Detected Stroke based on the classified temporal shift as determined by the classifier circuitry using the trained model and, in response to the real-time detection, outputting an alert generated by the classifier circuitry indicating Detected Stroke to at least one of an alert recipient transceiver, a local or remote server, or a user interface device.

* * * * *